(12) United States Patent
Matsuo et al.

(10) Patent No.: US 9,261,443 B2
(45) Date of Patent: Feb. 16, 2016

(54) METHOD FOR QUANTIFICATION OF SOLUBLE LR 11

(71) Applicant: SEKISUI MEDICAL CO., LTD., Tokyo (JP)

(72) Inventors: Masanao Matsuo, Ryugasaki (JP); Hiroyuki Ebinuma, Ryugasaki (JP); Isamu Fukamachi, Ryugasaki (JP); Hideaki Bujo, Chiba (JP); Yasushi Saito, Chiba (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 13/889,731

(22) Filed: May 8, 2013

(65) Prior Publication Data
US 2013/0302826 A1    Nov. 14, 2013

Related U.S. Application Data

(63) Continuation of application No. 12/933,818, filed as application No. PCT/JP2009/001176 on Mar. 17, 2009, now abandoned.

(30) Foreign Application Priority Data

Mar. 21, 2008   (JP) ................................. 2008-073047

(51) Int. Cl.
*G01N 33/53* (2006.01)
*G01N 1/34* (2006.01)
*C07K 16/28* (2006.01)
*G01N 33/92* (2006.01)

(52) U.S. Cl.
CPC ........ *G01N 1/34* (2013.01); *C07K 16/28* (2013.01); *G01N 33/92* (2013.01)

(58) Field of Classification Search
None
See application file for complete search history.

(56) References Cited

U.S. PATENT DOCUMENTS

| | | | |
|---|---|---|---|
| 5,352,583 A * | 10/1994 | Sakata et al. ................... | 435/7.4 |
| 5,420,016 A | 5/1995 | Boguslaski et al. | |
| 6,780,979 B1 * | 8/2004 | Deslys ........................... | 530/412 |
| 7,482,174 B2 * | 1/2009 | Kiefer et al. ................... | 436/529 |

FOREIGN PATENT DOCUMENTS

| | | |
|---|---|---|
| JP | 9 163988 | 6/1997 |
| WO | 2008 155891 | 12/2008 |

OTHER PUBLICATIONS

Zhu, Y. et al., "LR11, An LDL Receptor Gene Family Member, Is a Novel Regulator of Smooth Muscle Cell Migration.", Circulation Resarch, vol. 94, No. 6, pp. 752-758, (Apr. 2, 2004).
Ohwaki, K. et al., A Secreted Soluble Form of LR11 Specifically Expressed in Intimal Smooth Muscle Cells, Accelerates Formation of Lipid-Laden Macrophages, Arteriosoler Thromb. Vasc. Biol., vol. 27, No. 5, pp. 1050-1056, (May 16, 2007).
Matsuo, M. et al., "Development of ELISA Assay of Soluble LR11" DAI 40 KAI Japan Atherosclerosis Society Sokai-Gakujutsu Shukai Program. Shorokushu, p. 239, (Jun. 27, 2008) (with partial English translation).
Yamazaki, H. et al., "Elements of Neural Adhesion Molecules and a Yeast Vacuolar Protein Sorting Receptor Are Present in a Novel Mammalian Low Density Lipoprotein Receptor Family Member", The Journal of Biological Chemistry, vol. 271, No. 40, pp. 24761-24768, (Oct. 4, 1996).
Kanaki, T. et al., "Arteriosclerosis, Thrombosis, and Vascular Biology", Journal of the American Heart Association, pp. 2687-2695, (Nov. 1999).
Bujo, H. "Physiologically Active Substance Capable of Acting on Lesion of Arteriosclerosis or Lesion Formation Process and Condition of Disorder a Novel Biomarker of Intimal Smooth Muscle Cells: LR11", Igaku No. Ayumi, vol. 221, No. 13, pp. 1200-1203 (Jun. 30, 2007) (with partial English translation).
Jiang, M. et al., "Ang II-Stimulated Migration of Vascular Smooth Muscle Cells Is Dependent on LR11 in Mice", Research Article, The Journal of Clinical Investigation , http:// www.jci.org, vol. 118, No. 8, pp. 2733-2746 (Aug. 2008).
Masaki, T. et al., The 39th Annual Scientific Meeting of the Japan Atherosclerosis Society—Abstract, General Lecture Subject, (Poster) 189, p. 264 (Jun. 27, 2007) (with English translation).
International Search Report issued May 12, 2009 in PCT/JP09/001176 filed Mar. 17, 2009.

* cited by examiner

*Primary Examiner* — Gary W Counts
(74) *Attorney, Agent, or Firm* — Oblon, McClelland, Maier & Neustadt, L.L.P

(57) ABSTRACT

Provided is a method for quantifying soluble LR11 in a biological sample such as serum by an immunological means conveniently and accurately without the need of carrying out any complicated separation manipulation. An immunological quantification method for soluble LR11 in a sample derived from a mammal, including a step of treating the sample with at least one surfactant selected from a group consisting of a polyoxyalkylene alkyl ether, a polyoxyalkylene alkyl phenyl ether, an alkyl glycoside, an alkylthio glycoside, an acyl-N-methylglucamide and a salt of cholic acid.

7 Claims, 14 Drawing Sheets

METHOD FOR QUANTIFICATION OF SOLUBLE LR 11

This application is a Continuation of U.S. patent application Ser. No. 12/933,818 filed Sep. 21, 2010, now abandoned, which is a 371 of PCT/JP2009/001176 filed Mar. 17, 2009, which is incorporated herein by reference.

TECHNICAL FIELD

The present invention relates to a method for quantifying soluble LR11 in a sample derived from a mammal.

BACKGROUND ART

LDL receptor relative with 11 ligand-binding repeats (LR11) is a LDL receptor-analogous protein having a structure specific to LDL receptor family (Patent Document 1 and Non-Patent Document 1). It is known that, although hardly expressed in cells of normal blood vessel wall, the protein is recognized to be specifically expressed in thickened intimal smooth muscle cells (Non-Patent Document 2). It is also known that, according to the study using cultured smooth muscle cells, expression amount of LR11 increases in accordance with the proliferation of the smooth muscle cells, so that secretion of LR11 into a culture medium is recognized, and when LR11 gene is functionally impaired in a mouse model having defective cuff by using development engineering method, thickening of vascular intima caused by migration and proliferation of smooth muscle cells is inhibited (Non-Patent Document 3). Furthermore, it is recently found that, in addition to membrane-bound type LR11, a soluble LR11 which is fragmentized by a protease exists (Non-Patent Document 4). Still furthermore, it is reported that the soluble LR11 also exists in human blood (Non-Patent Document 5).

As a method of quantifying soluble LR11, a method in which soluble LR11 in a sample is separated by using an insoluble carrier to which a chaperone molecule RAP (receptor associated protein) having an affinity for LR11 is bonded and then the protein is subjected to SDS-PAGE and Western blot followed by detection based on immunostaining using an anti-LR11 antibody, etc. is known (Non-Patent Documents 5 and 6). However, the method requires a process of separating soluble LR11 from a sample, and therefore operation of the process is complicated.

PRIOR ART DOCUMENT

Patent Document 1: Japanese Patent Application Laid-Open (JP-A) No. H9-163988
Non-Patent Document 1: J. Biol. Chem. 1996; 271, p 24761-24768
Non-Patent Document 2: Arterioscler. Thromb. Vasc. Biol. 1999; 19, p 2687-2695
Non-Patent Document 3: Circ. Res. 2004; 94; p 752-758
Non-Patent Document 4: *IGAKU NO AYUMI*, Vol. 221, No. 13, p 1200-1203
Non-Patent Document 5: J Clin Invest. 2008; 118, p 2733-2746
Non-Patent Document 6: The 39$^{th}$ Annual Scientific Meeting of the Japan Atherosclerosis Society—Abstract, General lecture subject (poster) 189, p 264

DISCLOSURE OF THE INVENTION

Problem to be Solved by the Invention

Furthermore, the inventors of the present invention found that blood concentration of soluble LR11 is significantly higher in a patient suffering from arteriosclerotic disorder compared to a normal person, and reported that the measurement of the blood concentration of soluble LR11 could be a new marker for an arteriosclerotic disorder (Non-Patent Document 5 and Japanese Patent Application No. 2007-160225). For such diagnosis, development of a method for quantification of soluble LR11 by simple manipulation has been desired.

However, when an immunological measurement is carried out by using an antibody which reacts with soluble LR11 in a body fluid, for example in a system wherein a serum component is present, specifically, in serum or plasma as a subject, it was found that accurate quantification of soluble LR11 cannot be achieved due to influence of certain interfering substances.

Thus, object of the present invention is to provide a method for quantifying soluble LR11 in a biological sample such as serum by an immunological means conveniently and accurately without any complicated separating manipulation.

Means for Solving the Problem

Therefore, in order to accurately quantify soluble LR11 in body fluid, for example, even in a case where serum or plasma is taken as a sample for direct measurement, the inventors of the present invention studied various means for preventing the influence of impeding substances. As a result, it was found that, when a sample is treated with a certain kind of surfactant and then measurement is carried out based on an immunological measurement method, soluble LR11 in the sample can be quantified conveniently and accurately, and therefore the present invention was completed.

Specifically, the present invention provides an immunological method for measuring soluble LR11 in a sample derived from a mammal, including a step of treating the sample with at least one surfactant selected from a group consisting of a polyoxyalkylene alkyl ether, a polyoxyalkylene alkyl phenyl ether, an alkyl glycoside, an alkyl thioglycoside, an acyl-N-methylglucamide and a salt of cholic acid.

Furthermore, the present invention provides a kit for immunological measurement of soluble LR11, including an anti-soluble LR11 antibody and at least one surfactant selected from a group consisting of a polyoxyalkylene alkyl ether, a polyoxyalkylene alkyl phenyl ether, an alkyl glycoside, an alkylthio glycoside, an acyl-N-methylglucamine and a salt of cholic acid.

Furthermore, the present invention provides a use of a combination of an anti-soluble LR11 antibody and the specific surfactant described above for the manufacture of a kit for immunological measurement of soluble LR11.

Effect of the Invention

Based on the quantification method and with the immunological measurement kit of the present invention, concentration of soluble LR11 present in body fluid, for example, blood, can be conveniently measured with high sensitivity.

BEST MODE FOR CARRYING OUT THE INVENTION

Figure 1:
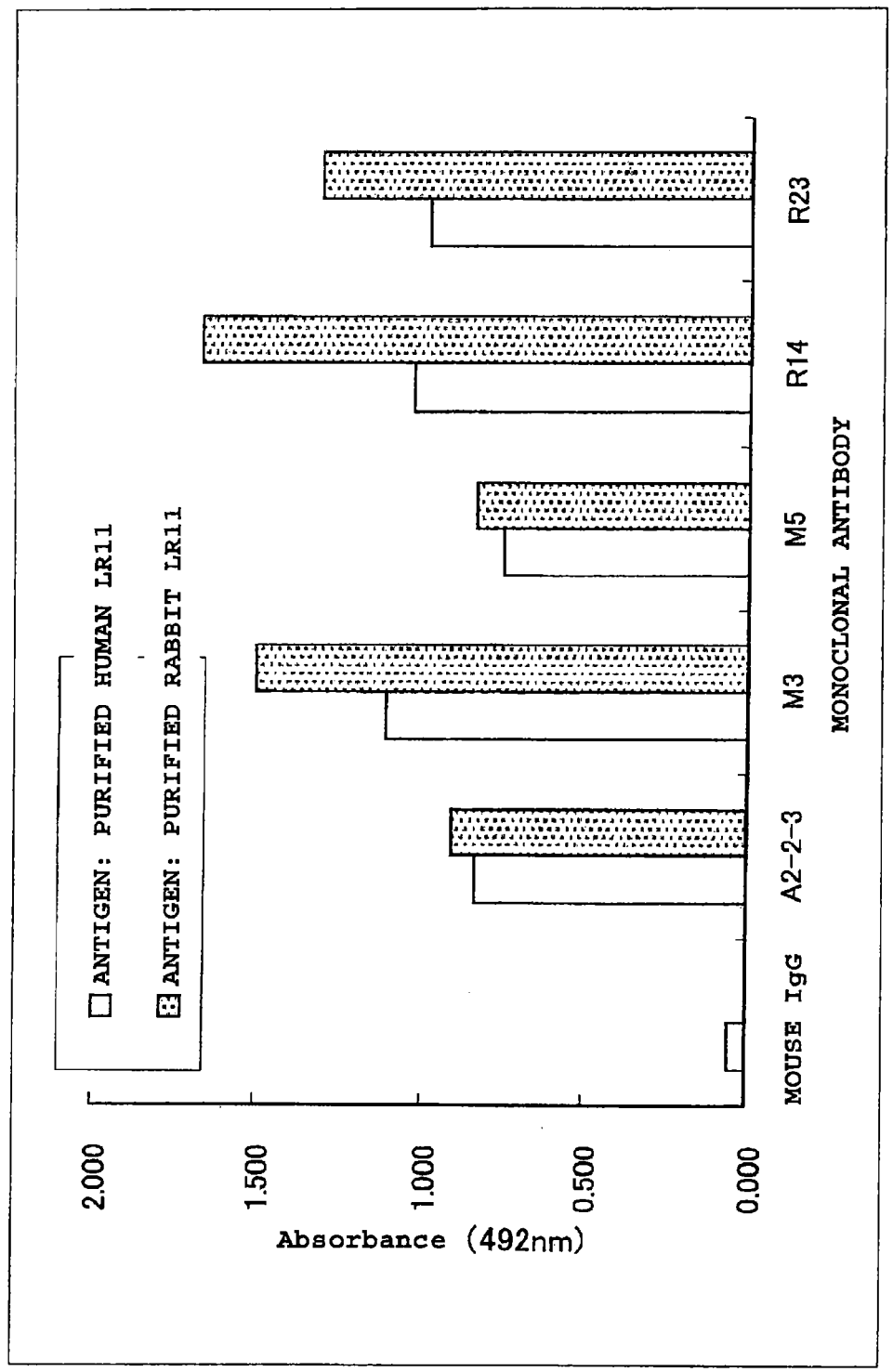
FIG. 1 shows a reaction of each monoclonal antibody against immobilized soluble LR11.

The quantification method of the present invention is a method of immunological quantification of soluble LR11 in a sample derived from a mammal. As for the mammal, a mammal including human such as human, monkey, horse, cow, pig, rabbit, rat, guinea pig, mouse and the like can be mentioned. As for the sample, a sample from a living body containing therein impeding substances (such as serum components) can be mentioned. Examples of the sample include blood, plasma and serum, as well as spinal fluid and urine.

The immunological quantification method of the present invention is not specifically limited as long as it is a method of quantifying soluble LR11 based on the reaction between an antigen and an antibody. However, from the viewpoint of avoiding influence of impeding substances in body fluid such as serum components, a quantification method using at least two kinds of antibody is preferable. In particular, a quantification method including a step of forming an immunocomplex by using at least two kinds of antibodies each having an antigen recognition site which is different from each other is preferable. According to the present invention, examples of the quantification method including a step of forming an immunocomplex by using at least two kinds of antibodies each having an antigen recognition site which is different from each other include sandwich ELISA or latex turbidimetric immunoassay (LTIA), etc.

Any kind of antibody including a monoclonal antibody and a polyclonal antibody may be used as the anti-soluble LR11 antibody, as long as it reacts with a soluble LR11 purified from serum. Particularly, the monoclonal antibody is preferably used. Preparation of the antibody may be carried out according the method known per se in the art.

For the preparation of a polyclonal antibody, a mouse, a rat, a hamster, a rabbit, a goat, a sheep, a chicken and the like are used as an animal to be immunized. The antiserum may be obtained after subcutaneously, intradermally or intraperitoneally administering an antigen to the animal once or several times. When a protein or a peptide is used as an antigen, immunization with a mixture containing therein fluid replacement which has an immunostimulating effect is more preferable.

Furthermore, preparation of a monoclonal antibody may be carried out according to a known method of preparing a monoclonal antibody, for example, in view of "Monoclonal Antibody" (written by Nagamune Hideaki and Terada Hiroshi, Hirokawa, 1990) or "Monoclonal Antibody" (James W. Golding, 3rd edition, Academic Press, 1996). In addition, the monoclonal antibody may be also prepared by DNA immunization method, and may be prepared in view of the literatures (Nature 1992 Mar. 12; 356, p 152-154 or J. Immunol. Methods March 1; 249, p 147-154).

As for the antigen that is used for the preparation of an antibody, LR11 protein or its partial fragment (i.e., peptide), or a vector containing cDNA which encodes LR11 protein or its partial fragment may be used. Examples of the partial fragment include the amino acid sequence that is represented by SEQ ID No. 1 or SEQ ID No. 2 described below can be mentioned. The amino acid sequence may include one or several deletions, substitutions or additions of the amino acids.

In order to obtain the monoclonal antibody which recognizes the conformation of LR11, a full-length LR11 vector, which is a construct including the full-length human LR11 gene, is the most appropriate antigen gene for immunization. However, other than that, a construct into which a gene encoding a partial fragment (i.e., peptide) of the LR11 protein is inserted may be also used as an antigen gene for immunization. DNA immunization may be carried out by subcutaneously injecting the gene construct described above singly or as a mixture to an animal (mouse or rat, etc.) based on any method of various gene transfer methods for immunizing an animal (for example, muscle injection, electroporation, or a method using gene gun, etc.) and by allowing the construct to get intracellularly transferred.

An example of preparing a monoclonal antibody using a peptide antigen is shown below as a reference.

(1) Production of a hybridoma

To the C-terminal of a synthetic peptide containing a partial amino sequence [432-447] of LR11 (SMNEENMRSVIT-FDKG) (SEQ ID No. 1), a cysteine residue is introduced. By using a cross-linking agent NBS (manufactured by Pierce Company), the synthetic peptide and KLH are linked to each other via lysine residue of KLH (Keyhole lympet hemocyanin) to provide an immunogen. This immunogen was mixed and emulsified with Complete Freund's Adjuvant (manufactured by GIBCO) in the ratio of 1:1 to give an emulsion of 0.1 mg/0.1 mL, and the emulsion was then subcutaneously administered 10 times with 1 week interval to a 6-week old female BALE/C mouse. Three days after the final immunization, the spleen was harvested. The spleen cells obtained from the harvested spleen and the SP2/O—Ag14 myeloma cells were admixed with each other with the ratio of 6:1. Then, in the presence of cell fusion reagent such as PEG/DMSO Solution (manufactured by Sigma), etc., cell fusion was carried out. The fused cells were suspended in HAT medium to have the spleen cell concentration of $2.5 \times 10^6$/mL, and then aliquoted (0.2 mL each) to a 96-well culture plate (manufactured by Corning). The cells were cultured in an incubator under 5% $CO_2$ at 37° C. Approximately two weeks later, the culture supernatant containing the grown hybridoma was subjected to ELISA shown below to determine the presence or absence of the antibody against the synthetic peptide (SEQ ID No. 1) described above. Consequently, a hybridoma cell line having higher possibility of producing the antibody was selected.

Specifically, the synthetic peptide (SEQ ID No. 1) described above was immobilized onto a micro plate (manufactured by NUNC®). IgG contained in each culture supernatant was added to the plate for the reaction, and consequently allowed to react with anti-mouse IgG goat antibody labeled with peroxidase. Subsequently, a peroxidase substrate solution containing ortho-phenylene diamine (manufactured by Tokyo Chemical industry, Co., Ltd.) was added for a color development reaction, and the color development was then stopped by adding 1.5 N sulfuric acid. The absorbance was measured by using micro plate reader (Abs. 492 nm). Accordingly, the hybridoma cell line showing the reactivity to the synthetic peptide was selected and the cloning was carried out based on a limiting dilution method. The final reactivity for LR11 was confirmed by reaction with the soluble LR11 which has been purified from serum as described below. As a result, anti-human soluble LR11 monoclonal antibody-producing hybridoma (A2-2-3) was established.

(2) Preparation of a Monoclonal Antibody

To a 12-week old female BALB/C mouse which had been intraperitoneally injected with 0.5 mL pristane two weeks before, the hybridoma cells obtained above were intraperitoneally administered ($0.5 \times 10^6$ cells). About 14 days later, ascites was collected and the supernatant was obtained by centrifuge. The supernatant was admixed with the same volume of the buffer solution for adsorption (3 mol/L NaCl-1.5 mol/L Glycine-NaOH, pH 8.5), and then filtered. The filtered solution was applied to the Protein A column (manufactured by GE Healthcare Bio Science), which had been equilibrated with the buffer solution for adsorption, to allow the adsorption of the antibody to the column. Thereafter, the antibody was eluted from the column by using 0.1 mol/L citric acid buffer (pH 3.0) to purify the anti-LR11 monoclonal antibody (A2-2-3 antibody).

In addition, an example of preparing a monoclonal antibody based on DNA immunization is given below as a reference.

(1) Construction of an Expression Vector

A partial gene fragment consisting of the full length LR11 gene (Q92673) (i.e., a gene encoding the peptide consisting of the amino acid sequence of LR11 [1000-1550] (SEQ ID No. 2)) was incorporated to a mammalian expression vector tagged with FLAG (pcDNA3.1, manufactured by Invitrogen). The expression vector contains a DNA which encodes the peptide consisting of GPI anchor sequence originating from human alkaline phosphatase. The resulting vector was named LR11 [1000-1550] vector.

(2) Determination of the Expression Product from CHO

By using the LR11 [1000-1550] vector constructed in the above, expression of a target gene product on the surface of cell membrane as intended was determined based on transient transfection expression test using CHO cells (originating from Chinese hamster ovary) before immunization. Specifically, one day before the test, the cells were plated to a 6-well plate ($1 \times 10^6$ cells per well). Under 5% $CO_2$, 37° C. condition, the cells were incubated overnight. On the transfection day, in a polystyrene round tube, a plasmid dilution solution (3 µg plasmid DNA+500 µL Dulbecco's Modified Eagle Medium (D-MEM)) and a diluted solution of lipofectamine-2000 (9 µL Lipofectamine-2000+500 µL D-MEM) were mixed well with each other. After the incubation at room temperature for 20 minutes, the culture supernatant of the cells plated a day before was discarded and the above mixture was gently added to the cells while being careful not to separate the cells from the plate. After the incubation under 5% $CO_2$, at 37° C. for 5 hours, the supernatant was removed and D-MEM medium containing 5% FCS was added. Then, the cells were cultured again at 5% $CO_2$, 37° C. condition for 24 hours.

Next day, the cells were removed from the plate by using a dissociation buffer (manufactured by Invitrogen) and used for the analysis by flow cytometry (FCM). FCM analysis was carried out as follows. Specifically, for primary antibody reaction, the cells were reacted with ANTI-FLAG (trade name) M2 antigen (SIGMA) in PBS buffer containing 3% FCS for 30 minutes at 4° C. The secondary antibody was washed with PBS buffer containing 3% FCS, and reacted with the PE-labeled anti-mouse IgG antibody (manufactured by Beckman) in PBS buffer containing 3% FCS for 30 minutes at 4° C. The cells were then washed with PBS buffer containing 3% FCS and suspended in an appropriate amount of PBS buffer containing 3% FCS. The resultant was supplied to a flow cytometer.

As a result, it was confirmed that, with the LR11 [1000-1550] vector that has been established as described above, the target gene product is indeed expressed on the cell surface.

(3) Antibody Production Based on DNA Immunization

Regarding the DNA immunization, gold particle-sensitized LR11 [1000-1550] vector described in section (1), either alone or in combinations thereof, was subcutaneously introduced to an animal to be immunized (mouse or rat) using a gene gun to transfer the vector into cells. Specifically, by using Helios (trade name) Gene Gun Optimization Kit (manufactured by Bio-Rad), gold particle-sensitized LR11 [1000-1550] vector (200 µg vector per 25 mg gold particles) was administered according to the manufacturer's instructions enclosed in the kit. The immunization was carried out for 4 times with 2-week intervals. At the time of the 4th immunization, a small amount of antiserum was sampled. The antiserum which had been diluted 1,000-fold with PBS containing 3% FCS was used as a primary antibody for the FCM analysis. In this case, the CHO cells which transiently express the target gene product described in the above section (2) (herein below, also referred to as cells for forced expression) were used for the FCM analysis. As a result, an increase in the antibody value was confirmed. Further, the production of monoclonal antibody was carried out according to a general cell fusion method. Specifically, after performing twice the final boost, the immunized animal was sacrificed and the antibody-producing cells were isolated according to a standard protocol, and the cells were subjected to the cell-fusion with mouse myeloma cells. As a result, the antibody-producing hybridoma cell line was prepared. After culturing this hybridoma cells, part of the culture supernatant was taken and an enzyme immunoassay using the cells for forced expression and FCM analysis were carried out. Consequently, the hybridoma cell lines which have a response to the antigen protein but not to the non-antigenic protein were selected.

In addition, the enzyme immunoassay using the cells for forced expression was carried out as follows. The cells for forced expression were coated on a 96-well plate and reacted with the culture supernatant of the hybridoma as a primary antibody. After the reaction with the primary antibody, the plate was washed and added with a secondary antibody. Herein, the secondary antibody indicates an antibody which can recognize the mouse immunoglobulin or the rat immunoglobulin of the primary antibody and corresponds to an antibody that is labeled with horse radish peroxidase (HRP). After the reaction, a fluorescent substrate for the enzyme that is labeled on the secondary antibody was added and the analysis was carried out using a fluorescence measurement plate reader.

Subsequently, the cloning was carried out for the selected hybridoma cell lines based on a limiting dilution method. As a result, the cell line recognized to be stable and to have high antibody value was selected as a hybridoma cell line for producing a monoclonal antibody.

Next, mass production of the monoclonal antibody from the ascites was carried out as follows. To a nude mouse which had been previously treated with 0.5 mL pristane, 0.5 mL phosphate buffered physiological saline (pH 7.4) containing the cloned hybridoma cells ($1 \times 10^6$ to $3 \times 10^6$ cells) was intraperitoneally injected. Approximately two weeks later, ascites was collected and the monoclonal antibody was purified by affinity column using Protein A.

Accordingly, the anti-soluble LR11 mouse monoclonal antibody (M3) and (M5) and the anti-LR11 rat monoclonal antibody (R14) and (R23) were obtained by DNA immunization. The reactivity for LR11 was finally confirmed based on the reactivity for the soluble LR11 that had been purified from the serum as described below. The above describes one example showing the production of a monoclonal antibody by DNA immunization.

According to the method of the present invention, immunological quantification is carried out after treating a sample with a specific kind of surfactant. With such treatment, influence of the substances which have a negative effect on quantification of soluble LR11 contained in a sample can be avoided.

The surfactant should be at least one substance selected from a group consisting of polyoxyalkylene alkyl ether, a polyoxyalkylene alkyl phenyl ether, an alkyl glycoside, an alkylthio glycoside, an acyl-N-methylglucamine and a salt of cholic acid.

Among these, polyoxyalkylene alkyl ether, polyoxyalkylene alkyl phenyl ether, alkyl glycoside, alkyl thioglycoside and acyl-N-methylglucamine are more preferable. Acyl-N-methylglucamine is particularly preferable.

As for the polyoxyalkylene alkyl ether and polyoxyalkylene alkylphenyl ether, polyoxyethylene $C_8$-$C_{24}$ alkyl ether and polyoxyethylene $C_8$-$C_{24}$ alkylphenyl ether are preferable. Specific examples include polyoxyethylene octyl ether, polyoxyethylene decyl ether, polyoxyethylene dodecyl ether, polyoxyethylene octyl phenyl ether, polyoxyethylene decyl phenyl ether, and polyoxyethylene dodecyl phenyl ether. Herein, the number of polyoxyethylene is preferably from 4 to 40. As a commercially available product of polyoxyethylene (10) octylphenyl ether, Triton X-100 (trade name) can be mentioned.

As for the alkylglycoside and alkylthioglycoside, $C_8$-$C_{24}$ alkylglucoside, $C_8$-$C_{24}$ alkylmaltoside, $C_8$-$C_{24}$ alkylthioglucoside and $C_8$-$C_{24}$ alkylthiomaltoside are preferable. Specific examples include n-octyl-β-D-glucoside, n-octyl-α-D-glucoside, n-octyl-β-D-maltoside, n-decyl-β-D-maltoside, n-decyl-β-D-maltoside, n-heptyl-β-D-thioglucoside, n-octyl-β-D-thioglucoside and n-nonyl-β-D-thiomaltoside. Among these, n-octyl-β-D-glucoside is preferable. As a commercially available product, n-octyl-β-D-glucoside (manufactured by Dojindo Laboratories), etc. can be mentioned. As for the cholic acid salt, examples include sodium cholate and potassium cholate.

As for the acyl-N-methylglucamine, $C_8$-$C_{24}$ alkanoyl-N-methylglucamine is preferable. Specific examples include octanoyl-N-methylglucamine, nonanoyl-N-methylglucamine and decanoyl-N-methylglucamine. Among these, octanoyl-N-methylglucamine or nonanoyl-N-methylglucamine is preferable. As a commercially available product of octanoyl-N-methylglucamine and nonanoyl-N-methylglucamine, MEGA-8 (manufactured by Dojindo Laboratories) and MEGA-9 (manufactured by Dojindo Laboratories, etc. can be mentioned, respectively.

As a means to treat a sample with a surfactant, the specific surfactant described above may be added to the sample before or during the immunological measurement. Preferably, the surfactant is added before the immunological measurement.

The use concentration of the surfactant may be appropriately decided depending on the type of the surfactant used. For example, it is 0.1 to 15% by mass, or preferably 2 to 10% by mass in a sample. The treatment temperature is 5 to 40° C., or preferably 10 to 30° C. The reaction time is 1 to 24 hrs, or preferably 6 to 20 hrs including the time for the treatment with the surfactant and the reaction between the antibody and the treated sample.

In addition, the sample is preferably diluted 1 (undiluted solution) to 50-fold, or preferably 4 to 30-fold. In this case, the dilution is preferably carried out by using a neutral to alkaline buffer solution having pH 7 to 10 of phosphate buffer, glycine buffer, carbonate buffer, Tris buffer and the like.

With a sample added with the specific surfactant described above, the immunological quantification using an anti-soluble LR11 antibody may be carried out using a general means.

As for the means of the immunological quantification, examples include immunostaining (Western blot), enzyme linked immunosorbent assay (ELISA), sandwich ELISA, immunoturbidimetry (TIA or LTIA), enzyme immunoassay, chemiluminescence immunoassay and fluorescence immunoassay.

When the soluble LR11 which reacts with the anti-soluble LR11 antibody is measured quantitatively or semi-quantitatively, it is preferable that results are compared to LR11 as a standard. As for the LR11 which may be used as a standard, for example, the serum-soluble LR11 with known concentration, the LR11 recovered from cultured cells or culture supernatant of smooth muscle cell or neuroblast cell line, a recombinant LR11, or a synthetic peptide used as an immunogen for the antibody production, etc. may be preferably used.

As an example of the immunological quantification described above, quantification based on sandwich ELISA is given below. For example, in an appropriate buffer solution, one type of the anti-soluble LR11 monoclonal antibody is immobilized on an insoluble carrier to give an immobilized antibody. As a secondary antibody, another anti-soluble LR11 monoclonal antibody which recognizes a recognition site different from the site that the aforementioned anti-soluble LR11 monoclonal antibody recognizes is labeled with an enzyme. By reacting them with a tested sample and measuring the activity of the enzyme that is linked to the secondary antibody, the soluble LR11 contained in the sample may be measured. In addition, by using biotinylated anti-soluble LR11 monoclonal antibody as a secondary antibody, performing the reaction with a tested sample and the reaction with enzyme-labeled avidin, and measuring the activity of the labeled enzyme, the LR11 contained in the sample may be also measured.

Examples of the insoluble carrier used above are preferably various synthetic polymers (e.g. polystyrene, polyethylene, and polypropylene), glass, silicone and insoluble polysaccharides (cross-linked dextran, polysaccharide), etc. These carriers may be used in the form of a sphere, a rod, fine particles, a test tube, a micro plate, etc. As for the condition for preparing an immobilized antibody, when a carrier in the form of a sphere, a rod or in a test tube or a micro plate is used, the concentration of the antibody is 1 to 10 μg/mL. When a carrier in the form of fine particles is used, the concentration of the antibody is 1 to 10 mg/mL. Further, it is preferable that a neutral to alkaline buffer solution having pH 7 to 10 of phosphate buffer, glycine buffer, carbonate buffer, Tris buffer, etc. is used and sensitization is performed at 4° C. to 25° C. for 1 to 72 hrs.

The enzyme-labeled antibody used may be prepared by a method known per se in the art. For example, according to the method by Nakane, et al, (Nakane P. K. et al, J. Histochem Cytochem, 22, p 1084-1089, 1974) or the method by Ishikawa, et al, (maleimide method: "Enzyme Immunoassay, $3^{rd}$ edition", IGAKU-SHOIN Ltd.), etc., a non-fragmentized immunoglobulin molecule as it is, which may be limitedly hydrolyzed by a suitable protease to give F(ab')$_2$ or Fab' if necessary, is labeled with an enzyme, by which the enzyme-labeled antibody may be prepared. Examples of the enzyme which may be used for labeling include peroxidase, alkaline phosphatase, β-D-galactosidase and glucose oxidase.

Biotinylated antibody may be also prepared by a method known per se in the art. However, by using a commercially available reagent for biotinylation (for example, Sulfo-NHS-Biotinylation Kit manufactured by Pierce Company), it may be more easily prepared.

The enzyme-labeled avidin may be also prepared by a method known per se in the art. However, a commercially available product may be also used (for example, StreptAvidin, Horseradish Peroxidase Conjugated manufactured by Pierce Company).

Furthermore, when the labeling material is an enzyme, a substrate and, if necessary, a color developing agent are used for measuring the activity of the enzyme. When peroxidase is used as an enzyme, hydrogen peroxide is used as a substrate, and as a color developing agent, o-phenylenediamine, 3,3',5,5'-tetramthylbenzidine, 2,2'-azinodi-[3-ethylbenzthiazoline-sulfonic acid]ammonium salt and the like may be used; when alkaline phosphatase is used as an enzyme, p-nitrophenyl phosphate, 3-(4-methoxyspiro {1,2-dioxetane-3,2'-tricyclo [3.3.1.1$^{3,7}$]dec ane}-4-yl)phenylphosphate: AMPPD, etc. may be used as a substrate; when β-D-galactosidase is used as an enzyme, β-D-galactopyranoside, 4-methylumbelliferyl-β-D-galactopyranoside, etc. may be used as a substrate, and; when glucose oxidase is used as an enzyme, β-D-glucose as a substrate in the co-presence of peroxidase and a color developing agent for peroxidase as a color developing agent may be used.

As shown in the Examples below, when a biological sample containing impeding substances that are same as the serum components is treated with the specific surfactant described above and immunological measurement is carried out by using the antibody which reacts with the soluble LR11, the soluble LR11 contained in the sample can be conveniently and accurately quantified. Thus, for carrying out the immunological measurement described above, the present invention may provide a kit in which the anti-soluble LR11 antibody and the above-described specific surfactant are contained in advance, i.e., a kit for the immunological measurement of the soluble LR11 including the antibody and the surfactant. Further, the anti-soluble LR11 antibody and the specific surfactant may be used for the manufacture of a kit for the immunological measurement of the soluble LR11.

The kit for the immunological measurement includes the anti-soluble LR11 antibody and the specific surfactant. These components may be present separately as a first reagent and a second reagent, or present in a mixture state. Furthermore, the kit may also include an optional component that is used for the detection of the soluble LR11, for example, a buffer solution, a stabilizing agent, or a reaction vessel, etc.

As described before, measurement of the soluble LR11 in blood may be a marker for an arteriosclerotic disorder. Thus, the kit may be used for evaluation of the presence or severity of the arteriosclerotic disorder.

Herein, the term "arteriosclerotic disorder" is a concept including disorders that are accompanied by progress of conditions caused by an arteriosclerotic lesion. Specific examples of the disorder include myocardial infarction, restenosis after percutaneous transluminal coronary angioplasty, cerebral infarction, cerebral hemorrhage, aneurysm, and arteriosclerosis obliterans. However, the disorder is not limited to them.

Furthermore, the term "evaluation of the presence or severity" is a concept that is not limited to a case in which an arteriosclerotic disorder has been already developed, and it is a concept also including a case in which possibility of future development into the disorder is determined.

As for the method for the evaluation of the presence or severity of the arteriosclerotic disorder, for example, it may be carried out by obtaining a biological sample from a mammal with suspected arteriosclerotic disorder, measuring the concentration of the soluble LR11 therefrom as described above while separately obtaining the concentration of the soluble LR11 in the same manner from a normal mammal group having no suspected arteriosclerotic disorder, and comparing those concentrations to evaluate the presence or severity of an arteriosclerotic disorder.

Herein, the term "normal" indicates an individual having no arteriosclerotic disorder. Regarding an objective indicator for an arteriosclerotic disorder, in human, it indicates no previous history of suffering from an arteriosclerotic disorder such as coronary occlusion, etc. and, for example, a normal blood pressure according to the "Year 2004 Guidelines for Treating Hypertension" by the Japanese Hypertension Society (i.e., systolic blood pressure of less than 130 mmHg and diastolic blood pressure of less than 85 mmHg); a normal type based on "Committee report regarding the criteria for classification and diagnosis of diabetes (1999)" by Japan Diabetes Society (i.e., fasting blood sugar level of less than 110 mg/dl) and; no relation with the "Diagnostic criteria for hyperlipidaemia (2002)" by Japan Atherosclerosis Society (i.e., regarding the lipid value obtained from serum taken when fasting, total cholesterol is less than 220 mg/dl, LDL cholesterol is less than 140 mg/dl, HDL cholesterol is 40 mg/dl or above, and triglyceride is less than 150 mg/dl).

In addition, by monitoring a change in the concentration of the soluble LR11 with time by using the kit of the present invention, effectiveness of a treatment using a pharmaceutical agent, etc. may be also determined.

The determination may be carried out based on a change in the concentration of the soluble LR11. For example, when there is an increasing tendency, it is determined that the disorder (for example, an arteriosclerotic disorder) has progressed. On the other hand, when there is a tendency showing a decrease or a flat response, it is determined that the progress of the disorder has been inhibited.

EXAMPLES

Herein below, the present invention will be explained in greater detail in view of the examples. However, it is evident that the present invention is not limited to them.

Reference Example 1

Purification of the Soluble LR11 from Rabbit Serum or Human Serum was Carried Out as Follows (Purification of the Soluble LR11)
*E. coli* DH5a transformed with the vector pGEX2T (manufactured by GE Healthcare Bio Science) to which human RAP gene is transferred was cultured and the cells were collected by centrifuge. The cells collected from the 3 L culture medium were suspended in phosphate buffer (pH 7.2) containing lysozyme and the surfactant TritonX-100 (trade name), and then disrupted by ultrasonication. The RAP/GST fusion protein contained in the supernatant obtained through centrifugation of the disrupt solution was passed through 10 mL Glutathione Sepharose 4 FF (manufactured by GE Healthcare Bio Science) for adsorption. After washing with phosphate buffer (PBS, pH 7.2), RAP-Sepharose resin was prepared.

The resulting RAP-Sepharose resin (10 mL) was mixed with either the rabbit serum or the human serum (1 L). After the overnight reaction under mild stirring at 4° C., the RAP-Sepharose resin was recovered and washed with phosphate buffer (pH 7.2) for each case. Next, the rabbit soluble LR11 or the human soluble LR11 was eluted by using citrate buffer (pH 5.0) followed by concentration. Then, the dialysis against phosphate buffer (pH 7.2) was performed, and the product was obtained as purified rabbit soluble LR11 or purified human soluble LR11.

Example 1

1) Reactivity of the Soluble LR11 Purified from Serum with the Monoclonal Antibody Reactivity of each monoclonal antibody with the immobilized soluble LR11 was confirmed as follows. First, to a micro plate (manufactured by NUNC®), a solution in which the purified rabbit soluble LR11 (Lot. 061208) was diluted 100-fold with 20 mM phosphate buffer having pH 7.2 (PBS) or a solution in which the purified human soluble LR11 (Lot. 061208) was diluted 20-fold with PBS was added in an amount of 50 μL/well to perform overnight immobilization of each soluble LR11. The resultant was washed with 20 mM phosphate buffer having pH 7.2 (BSA-PBST) and containing 0.05% Tween20 (trade name), followed by addition of 20 mM phosphate buffer having pH 7.2 (BSA-PBST) and containing 1% BSA and 0.05% Tween20 (trade name) (100 μL per well) to perform blocking at room temperature for 1 hr. After washing with PBST, 50 μL of the antibody solution in which each of the monoclonal antibody A2-2-3, M3 and R14 labeled with biotin using the biotinylating agent (manufactured by Pierce Company) had been diluted with BSA-PBST to have concentration of 10 μg/mL was added, and then the reaction was carried out at room temperature for 2 hrs. After washing with PBST, 50 μL solution in which peroxidase-labeled streptavidin (manufactured by Pierce Company) had been diluted with BSA-PBST to have concentration of 0.2 μg/mL was added, and the reaction was carried out at room temperature for 2 hrs. After washing with PBST, 50 μL of OPD substrate solution (0.1 M citrate buffer having pH 5.0 and containing 20 mM ortho-phenylene diamine and 12 mM hydrogen peroxide) was added and the reaction was carried out at room temperature for 10 minutes. Then, 50 μL of 1.5 N sulfuric acid was added to stop the color development. Then, the measurement was carried out by using a micro plate reader (Abs. 492 nm). In addition, as a negative control for measuring the reactivity of the antibody, mouse IgG was used.

As a result (FIG. 1), while the mouse IgG as a negative control hardly reacted to both the immobilized rabbit soluble LR11 and the immobilized human soluble LR11, the monoclonal antibody A2-2-3, M3, M5, R14 and R23 reacted to them.

2) ELISA Measurement System

Each of the monoclonal antibody A2-2-3, M3, M5, R14 or R23 was diluted with PBS to 5 μg/mL, added to a micro plate (manufactured by NUNC) to have 50 μL per well, and then immobilized overnight. In addition, as a negative control, mouse IgG was also immobilized. After washing with PBST, BSA-PBST was added in an amount of 100 μL per well to perform blocking at room temperature for 1 hr. After washing with PBST, a solution in which the purified rabbit soluble LR11 (Lot. 061208) had been diluted 25-fold with BSA-PBST or a solution in which the purified human soluble LR11 (Lot. 061208) had been diluted 25-fold with BSA-PBST was added in an amount of 50 μL/well, followed by reaction at room temperature for 2 hrs. After washing with PBST, 50 μL of the antibody solution in which each of the monoclonal antibody A2-2-3, M3, M5, R14 or R23 which had been labeled with biotin and diluted with BSA-PBST to have concentration of 10 μg/mL was added, and the reaction was carried out at room temperature for 2 hrs (as a negative control, biotinylated mouse IgG was used). After washing with PBST, 50 μL of the solution in which peroxidase-labeled streptavidin (manufactured by Pierce Company) had been diluted with BSA-PBST to have concentration of 0.2 μg/mL was added, and the reaction was carried at room temperature for 2 hrs. After washing with PBST, 50 μL of the OPD substrate solution was added and the reaction was carried out at room temperature for 10 minutes. Then, 50 μL of 1.5 N sulfuric acid was added to stop the color development. Then, the measurement was carried out by using a micro plate reader (Abs. 492 nm).

As a result, as shown in Table 1 and Table 2, it was found that the purified rabbit soluble LR11 and human soluble LR11 in liquid phase are detected from the sandwich ELISA system having the combination of monoclonal antibodies shown below.

TABLE 1

Monoclonal antibody-monoclonal antibody sandwich ELISA (antigen: purified human LR11)

| | | Antibody in liquid phase | | | | | |
|---|---|---|---|---|---|---|---|
| | | Mouse IgG | A2-2-3 | M3 | M5 | R14 | R23 |
| Immo-bilized antibody | Mouse IgG | −0.003 | 0.015 | 0.024 | 0.007 | −0.017 | −0.020 |
| | A2-2-3 | 0.003 | 0.110 | 0.432 | 0.449 | 0.693 | 0.690 |
| | M3 | 0.001 | 1.075 | 0.029 | 1.017 | 2.061 | 1.915 |
| | M5 | −0.001 | 0.150 | 0.158 | 0.079 | 0.308 | 0.309 |
| | R14 | −0.004 | 1.130 | 0.861 | 0.870 | −0.012 | 0.422 |
| | R23 | −0.002 | 0.878 | 1.264 | 1.165 | −0.005 | 0.007 |

Absorbance (492 nm)

TABLE 2

Monoclonal antibody-monoclonal antibody sandwich ELISA
(antigen: purified rabbit LR11)

| | | Antibody in liquid phase | | | | | |
|---|---|---|---|---|---|---|---|
| | | Mouse IgG | A2-2-3 | M3 | M5 | R14 | R23 |
| Immobilized antibody | Mouse IgG | 0.043 | −0.017 | −0.017 | −0.017 | −0.019 | −0.026 |
| | A2-2-3 | −0.004 | 0.007 | 1.898 | 0.856 | 1.822 | 1.212 |
| | M3 | −0.001 | 2.552 | 0.003 | 1.915 | 2.867 | 2.895 |
| | M5 | −0.007 | 0.229 | 0.300 | 0.144 | 0.535 | 0.361 |
| | R14 | −0.009 | 2.032 | 1.119 | 1.029 | 0.002 | 0.058 |
| | R23 | −0.009 | 1.579 | 2.475 | 1.833 | 0.005 | 0.041 |

Absorbance (492 nm)

Immobilized antibody A2-2-3-antibody in liquid phase M3, M5, R14, R23

Immobilized antibody M3-antibody in liquid phase A2-2-3, M5, R14, R23

Immobilized antibody M5-antibody in liquid phase A2-2-3, M3, R14, R23

Immobilized antibody R14-antibody in liquid phase A2-2-3, M3, M5, R23

Immobilized antibody R23-antibody in liquid phase A2-2-3, M3, M5

3) Measurement of the Purified LR11 Based on Sandwich ELISA

To a micro plate (manufactured by NUNC®), monoclonal antibody M3 which has been diluted with PBS to have 5 μg/mL was added (50 μL per well), and the immobilization was carried out at room temperature for 2 hrs. After washing with PBST, BSA-PBST was added in an amount of 100 μL per well for blocking at room temperature for 1 hr. After washing with PBST, a solution in which the rabbit soluble LR11 or the human soluble LR11 purified though the method described in the above-Reference example 1 was diluted with BSA-PBST to perform reaction. After washing with PBST, biotinylated monoclonal antibody R14 which had been diluted with BSA-PBST to have 5 μg/mL was added thereto to perform the reaction. After washing with PBST, peroxidase-labeled streptavidin (manufactured by Pierce Company) which had been diluted with BSA-PBST to have concentration of 0.2 μg/mL was reacted with the antibody. After washing with PBST, TMB substrate solution (0.1 M citrate buffer having pH 3.7 and containing 0.3 mg/mL of 3,3'-5,5'-tetramethyl-benzidine dihydrochloride (manufactured by Sigma) and 12 mM hydrogen peroxide) was added thereto in an amount of 50 μL to allow the color development for 30 min at room temperature. Then, 50 μL of 1.5 N sulfuric acid was added to stop the color development. Then, the measurement was carried out by using a micro plate reader (Abs. 450 nm).

Figure 2:
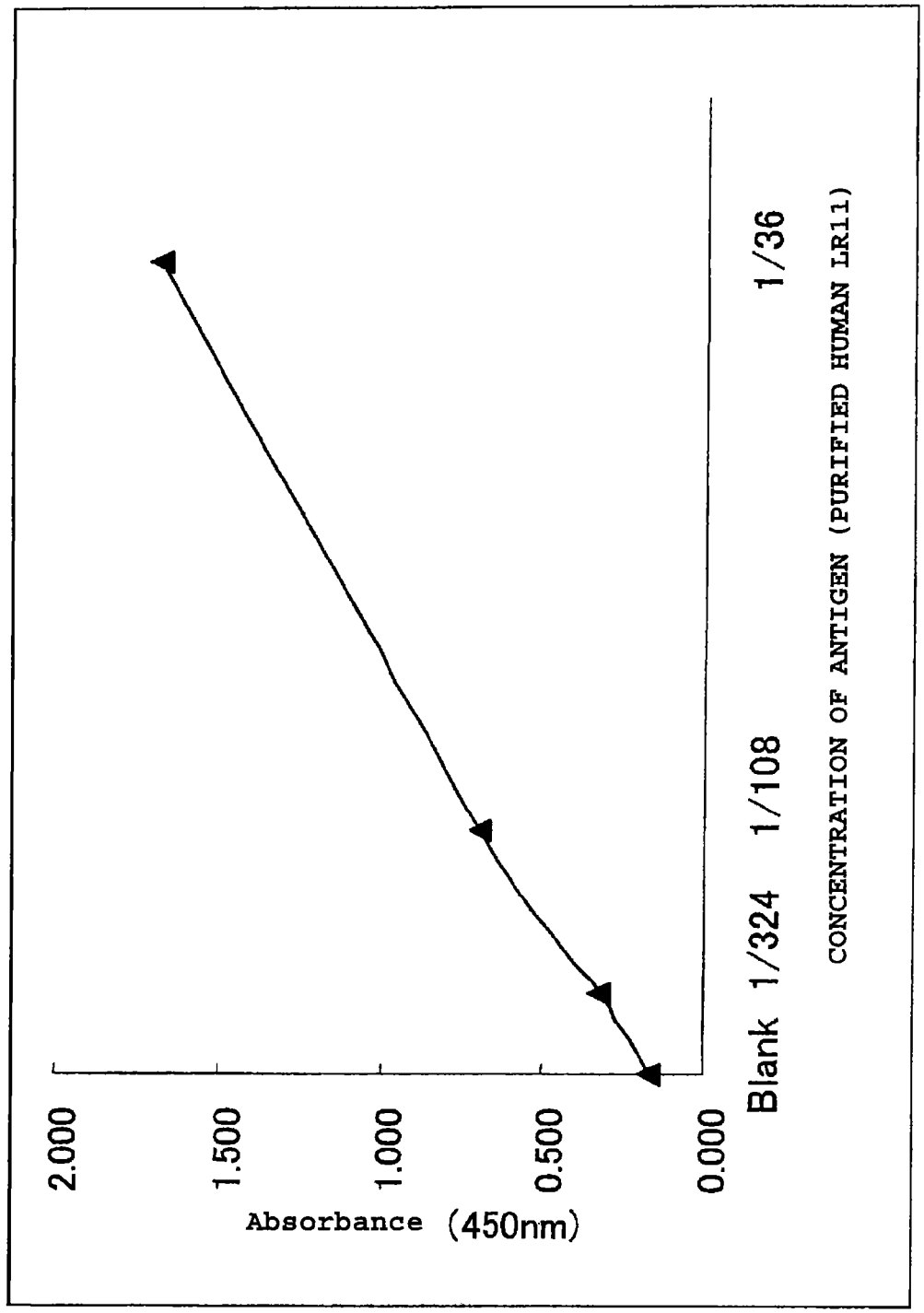
FIG. 2 shows a measurement of purified human soluble LR11 by sandwich ELISA.
Figure 3:
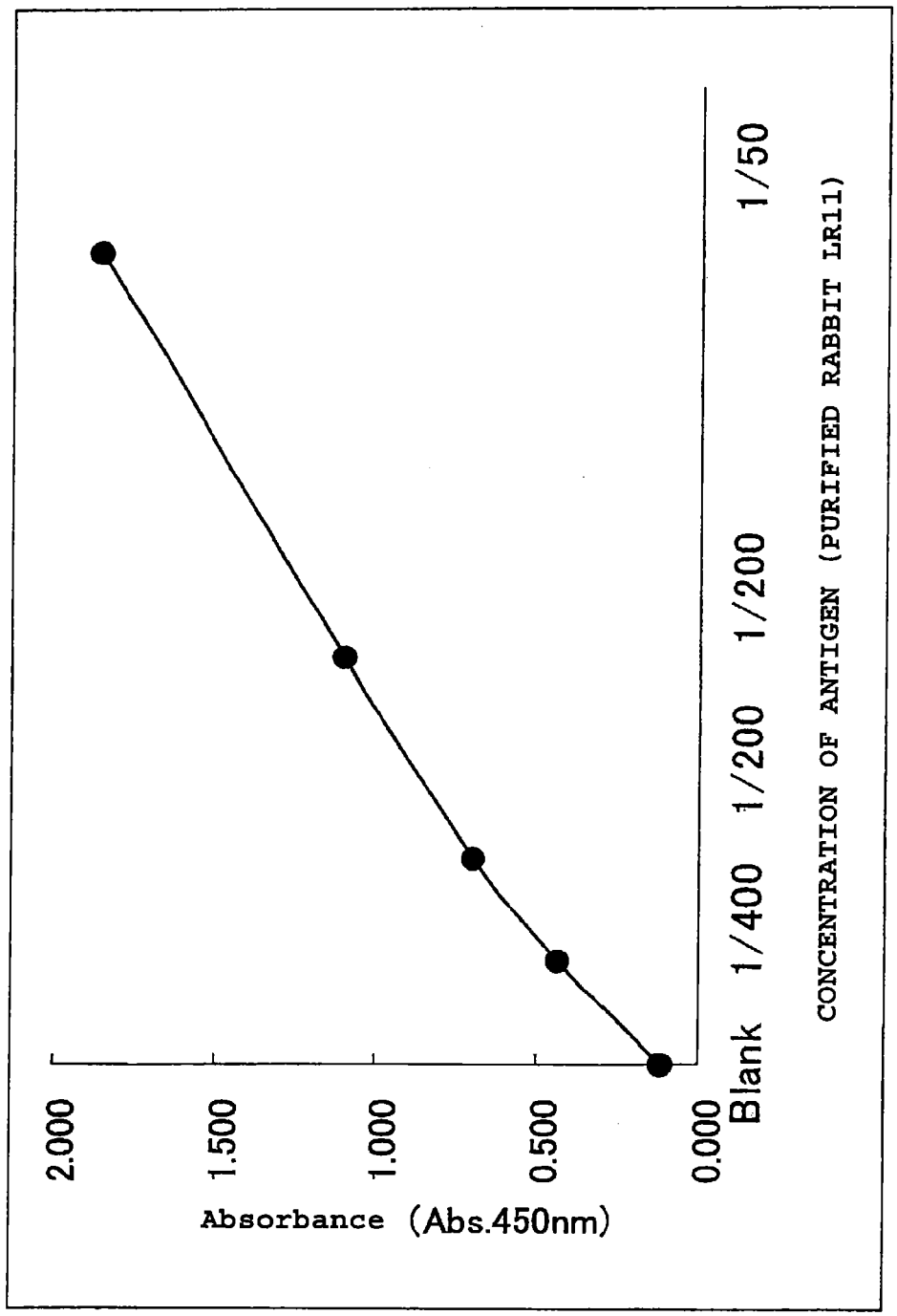
FIG. 3 shows a measurement of purified rabbit soluble LR11 by sandwich ELISA.

As shown in FIG. 2 and FIG. 3, it was confirmed that, by using the purified soluble LR11, the antigen concentration-dependent reaction can be obtained according to the variation in concentration of the antigen, i.e., human soluble LR11 or rabbit soluble LR11.

4) Effect of the Serum on ELISA System

First, to a micro plate (manufactured by NUNC®), monoclonal antibody M3 which had been diluted with PBS to have 5 μg/mL was added (50 μL per well), and the immobilization was carried out at room temperature for 2 hrs. After washing with PBST, BSA-PBST was added in an amount of 100 μL per well to perform blocking at room temperature for 1 hr.

After washing with PBST, a solution in which the purified rabbit soluble LR11 (Lot. 070601) had been diluted 100-, 200- or 400-fold with BSA-PBST or a solution in which the purified rabbit soluble LR11 (Lot. 070601) had been diluted 100-, 200- or 400-fold with human serum was added in an amount of 50 μL, respectively, followed by reaction at room temperature for 2 hrs.

After washing with PBST, 50 μL of biotinylated monoclonal antibody R14, which had been diluted with BSA-PBST to have 5 μg/mL, was added thereto for the reaction for 2 hrs at room temperature. After washing with PBST, peroxidase-labeled streptavidin (manufactured by Pierce Company) which had been diluted with BSA-PBST to have concentration of 0.2 μg/mL was added in an amount of 50 μL and the reaction was carried out at room temperature for 2 hrs. Subsequently, 50 μL of the TMB substrate solution was added to allow the color development for 30 min at room temperature.

Then, 50 μL of 1.5 N sulfuric acid was added to stop the color development. Then, the measurement was carried out by using a micro plate reader (Abs. 450 nm).

Figure 4:
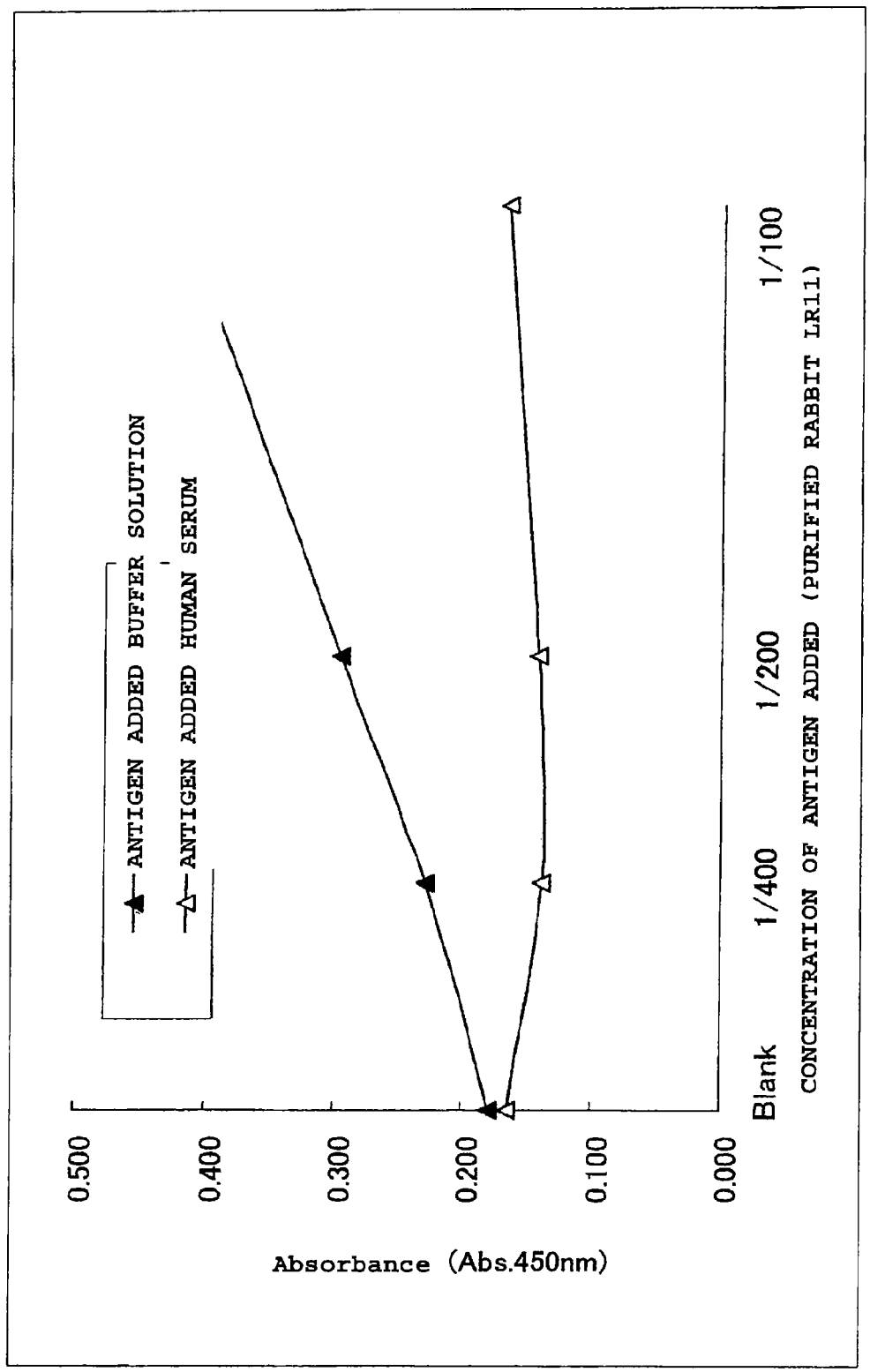
FIG. 4 shows an influence of serum in ELISA system.

As shown in FIG. 4, concentration-dependent reaction was observed for the rabbit soluble LR11 diluted in the buffer solution, while reaction of the rabbit soluble LR11 diluted in the human serum was inhibited under the influence of the serum components, and therefore no detection can be made.

Further, even for any of the combination of the antibodies of the above section 2) from which purified rabbit soluble LR11 and human soluble LR11 in liquid phase were detected, no detection can be made due to the influence of the serum components. Thus, without being limited to a combination of specific kinds of antibodies, the influence of the serum components was recognized.

5) Avoidance of the Influence of the Serum Components Based on Treatment with Surfactant To a micro plate (manufactured by NUNC®), monoclonal antibody M3 which had been diluted with PBS to have 5 μg/mL was added (50 μL per well), and the immobilization was carried out at room temperature for 2 hrs.

After washing with PBST, BSA-PBST was added in an amount of 100 μL per well to perform blocking at room temperature for 1 hr. After washing with PBST, human serum in which the purified rabbit soluble LR11 (Lot. 070601) had been added so as to obtain dilution of 50-, 100- or 200-fold at the time of the reaction (human serum was diluted to obtain dilution of 10-fold at the time of the reaction) was reacted in an amount of 50 μL per well (PBS for blank) at room temperature (15° C. to 25° C.) for 2 hrs in the presence of each of the surfactants of Tween20 (trade name), Triton-X100 (trade name), octanoyl-N-methylglucamine (MEGA-8), nonanoyl-N-methylglucamine (MEGA-9), sodium cholate and n-octyl-β-D-glucopyranoside (3.6% concentration for each).

After washing with PBST, 50 μL of a standard antibody solution in which biotinylated anti-human soluble LR11 monoclonal antibody R14 is diluted with BSA-PBST to have 5 μg/mL was added to the above (50 μL per well) for the reaction for 4 hrs at room temperature. After washing with PBST, peroxidase-labeled streptavidin (manufactured by Pierce Company) which has been diluted with BSA-PBST to have concentration of 0.2 μg/mL was added to the well (50 μL per well) and the reaction was carried out for 2 hrs at room temperature.

Subsequently, after washing with PBST, the TMB substrate solution was added to the well (50 μL per well) to allow the color development for 30 min at room temperature. Then, 1.5 N sulfuric acid was added in an amount of 50 μL per well to stop the color development. Then, the measurement was carried out by using a micro plate reader (Abs. 450 nm).

Figure 5:
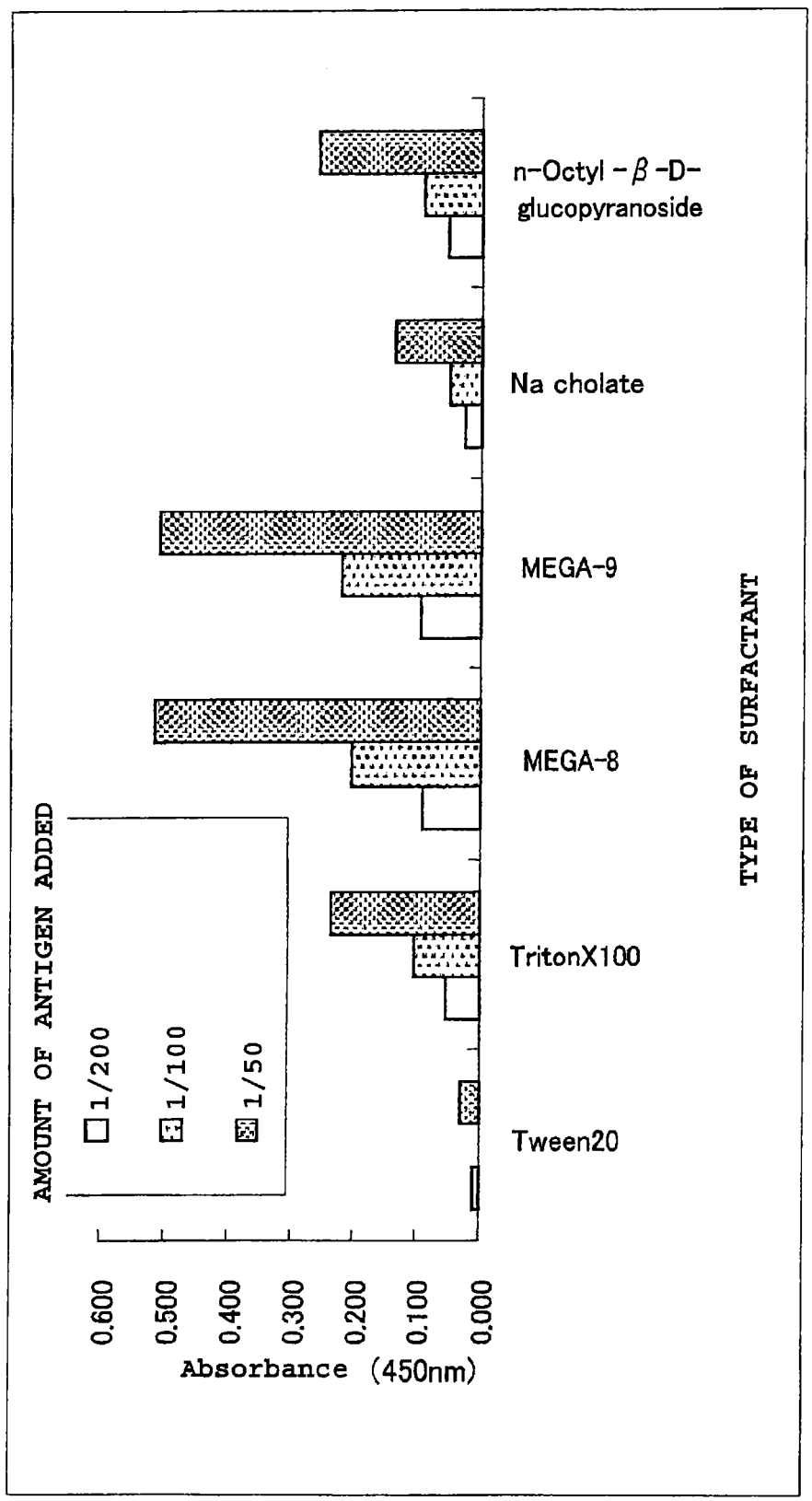
FIG. 5 shows avoidance of influence of serum components by treatment with surfactant.

As shown in FIG. 5, in case where the surfactant Tween20 (trade name) was used, influence of the serum components could not be avoided. However, in case where Triton-X100 (trade name), MEGA-8, MEGA-9, sodium cholate or n-octyl-β-D-glucopyranoside was used, even in the presence of the serum components, a reaction which is dependent on the concentration of the added rabbit soluble LR11 (Lot. 070601) was obtained. Such effect was particularly significant for MEGA-8 and MEGA-9. Meanwhile, FIG. 5 was obtained after subtracting the reagent blank value.

Example 2

Concentration Variation of MEGA-9

Figure 6:
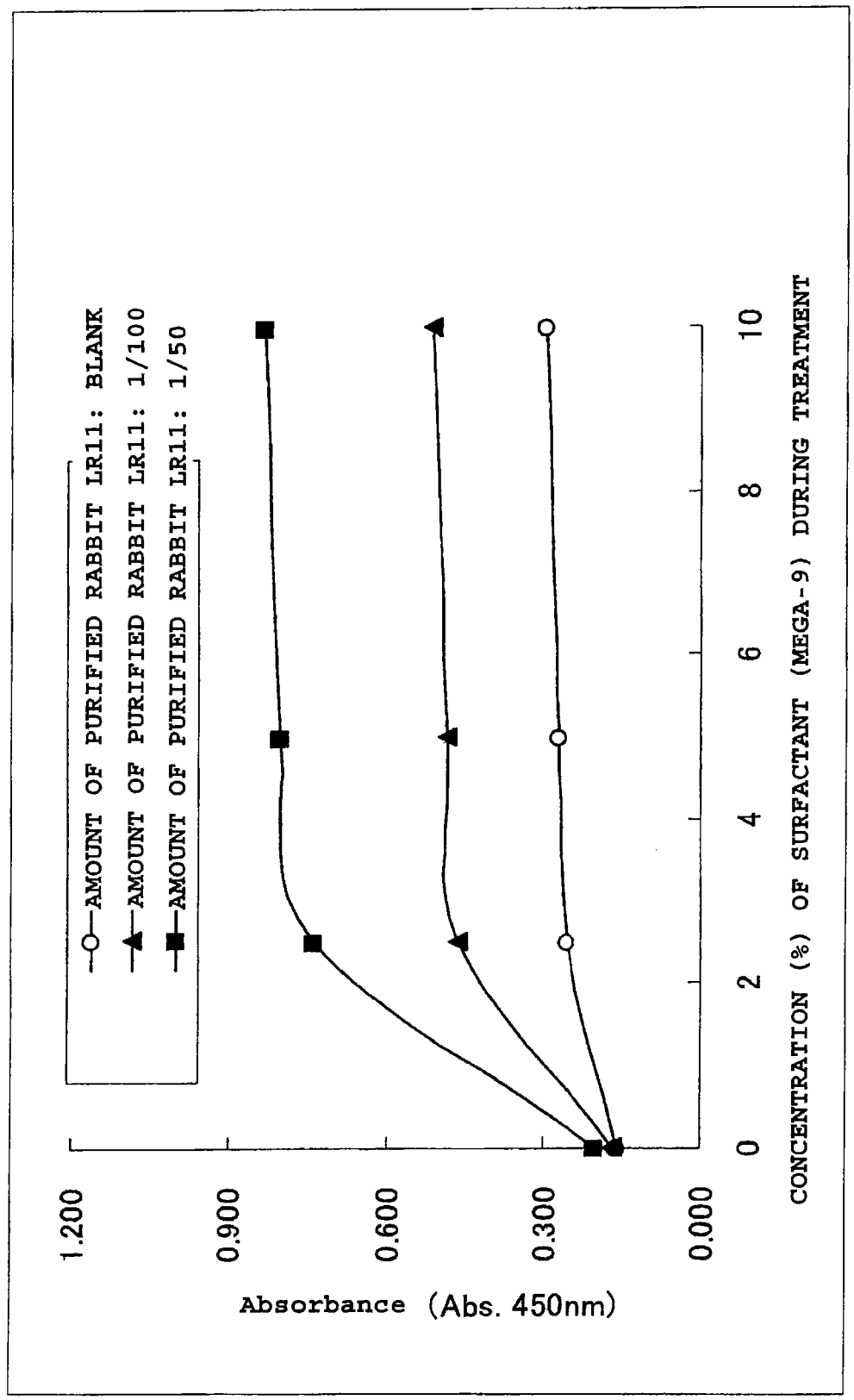
FIG. 6 shows a concentration of the surfactant (MEGA-9) effective for removing influence of the serum components.
Figure 7:
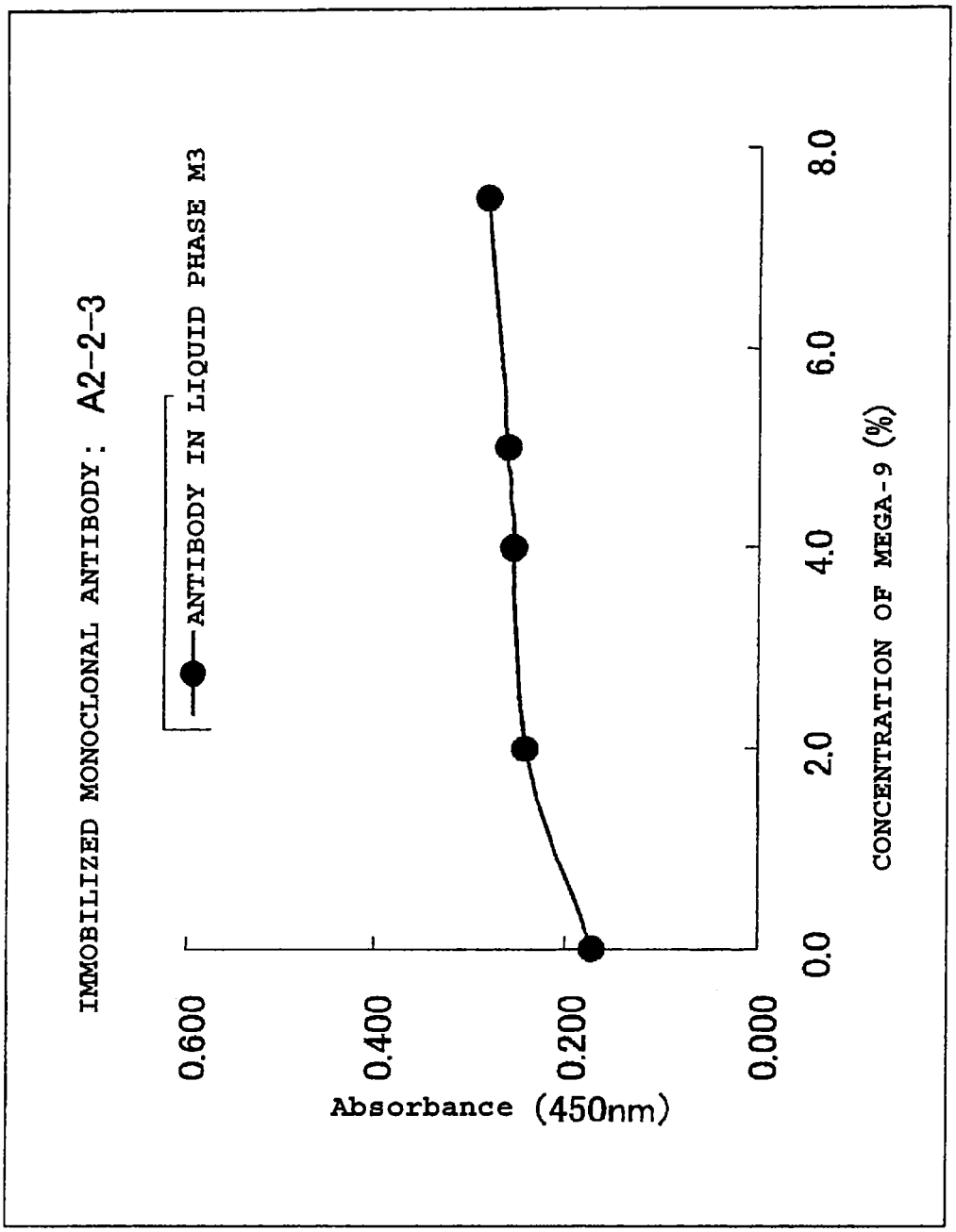
FIG. 7 shows a sandwich ELISA using the immobilized monoclonal antibody A2-2-3.
Figure 8:
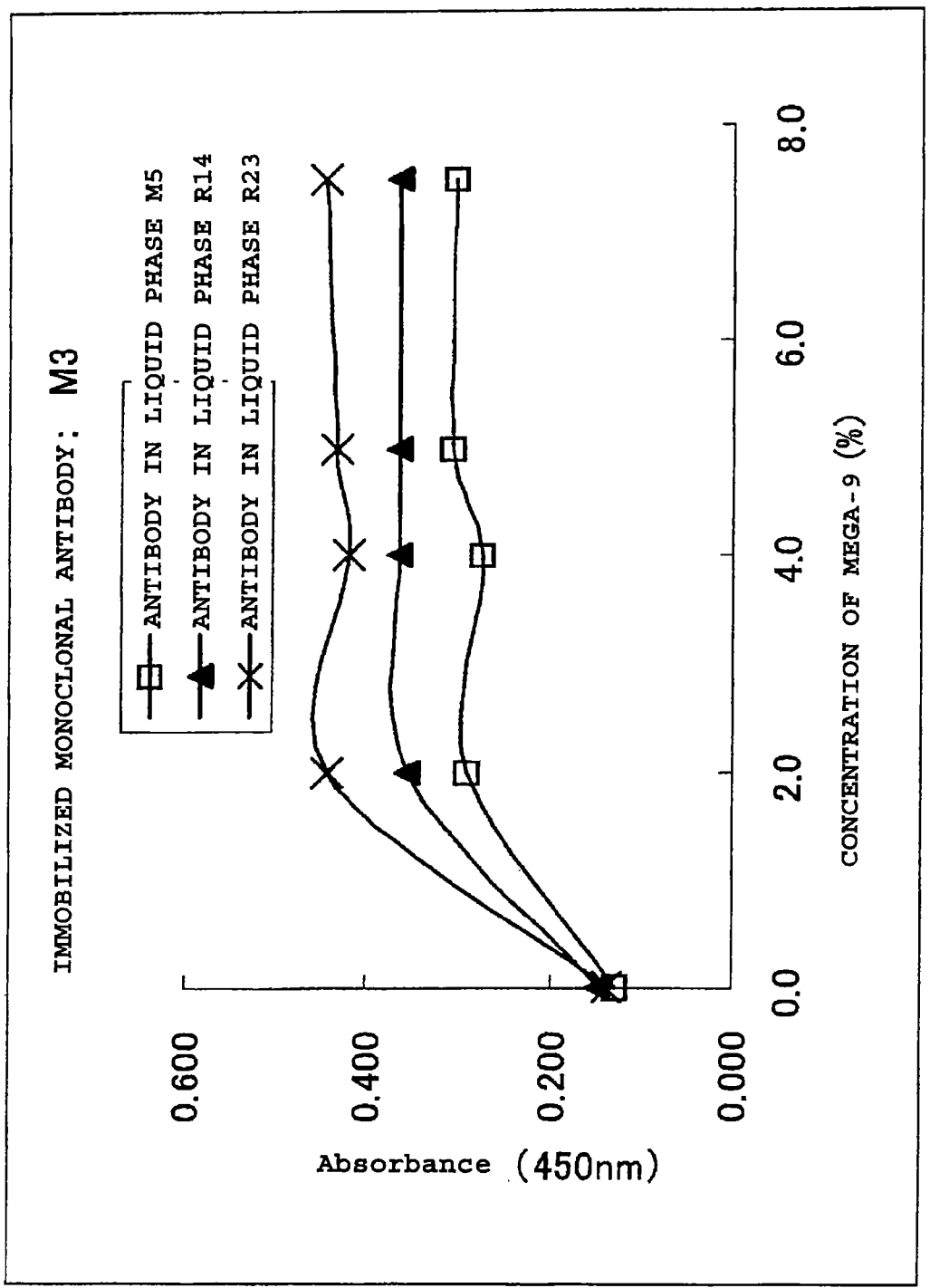
FIG. 8 shows a sandwich ELISA using the immobilized monoclonal antibody M3.
Figure 9:
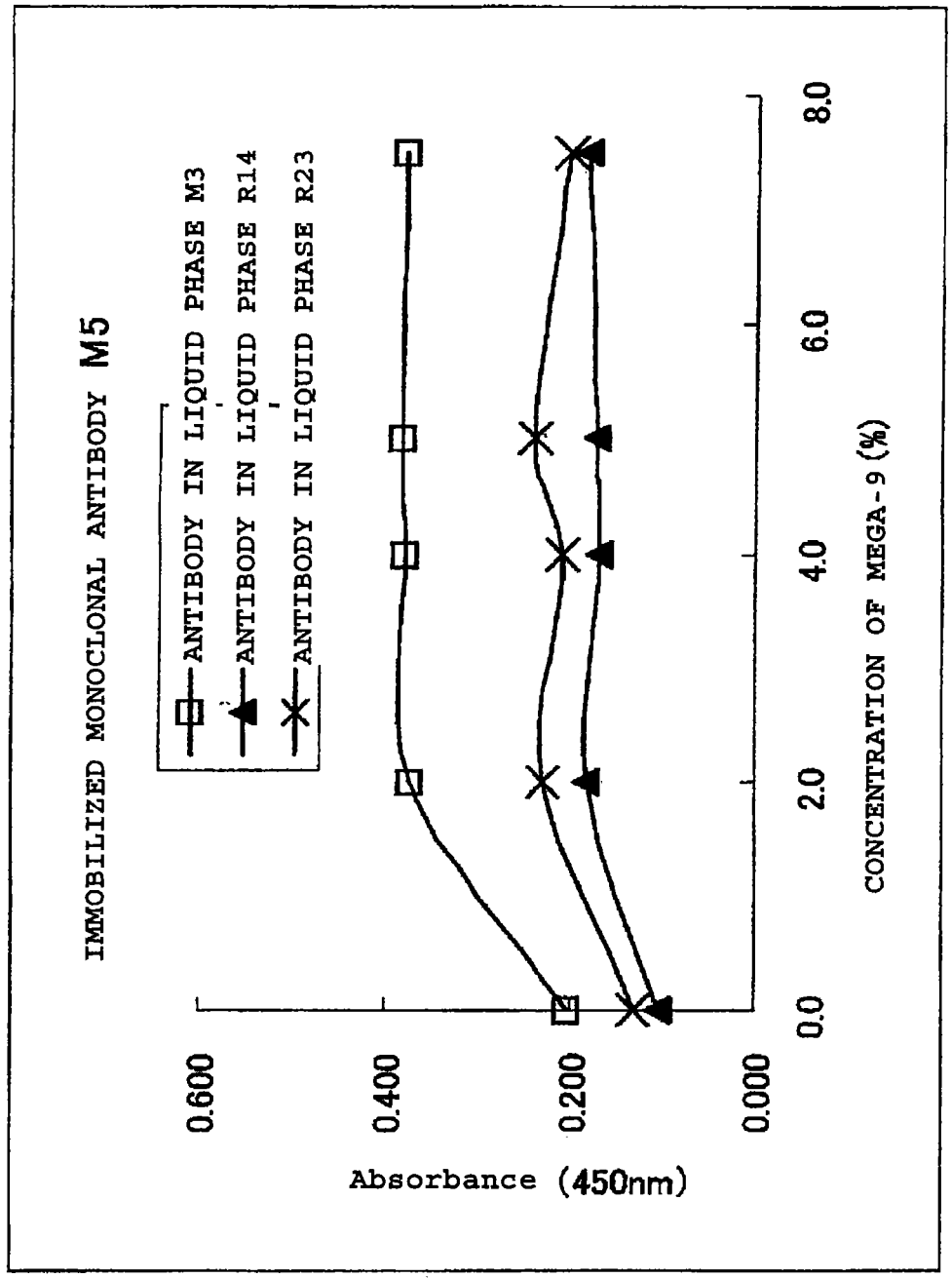
FIG. 9 shows a sandwich ELISA using the immobilized monoclonal antibody M5.
Figure 10:
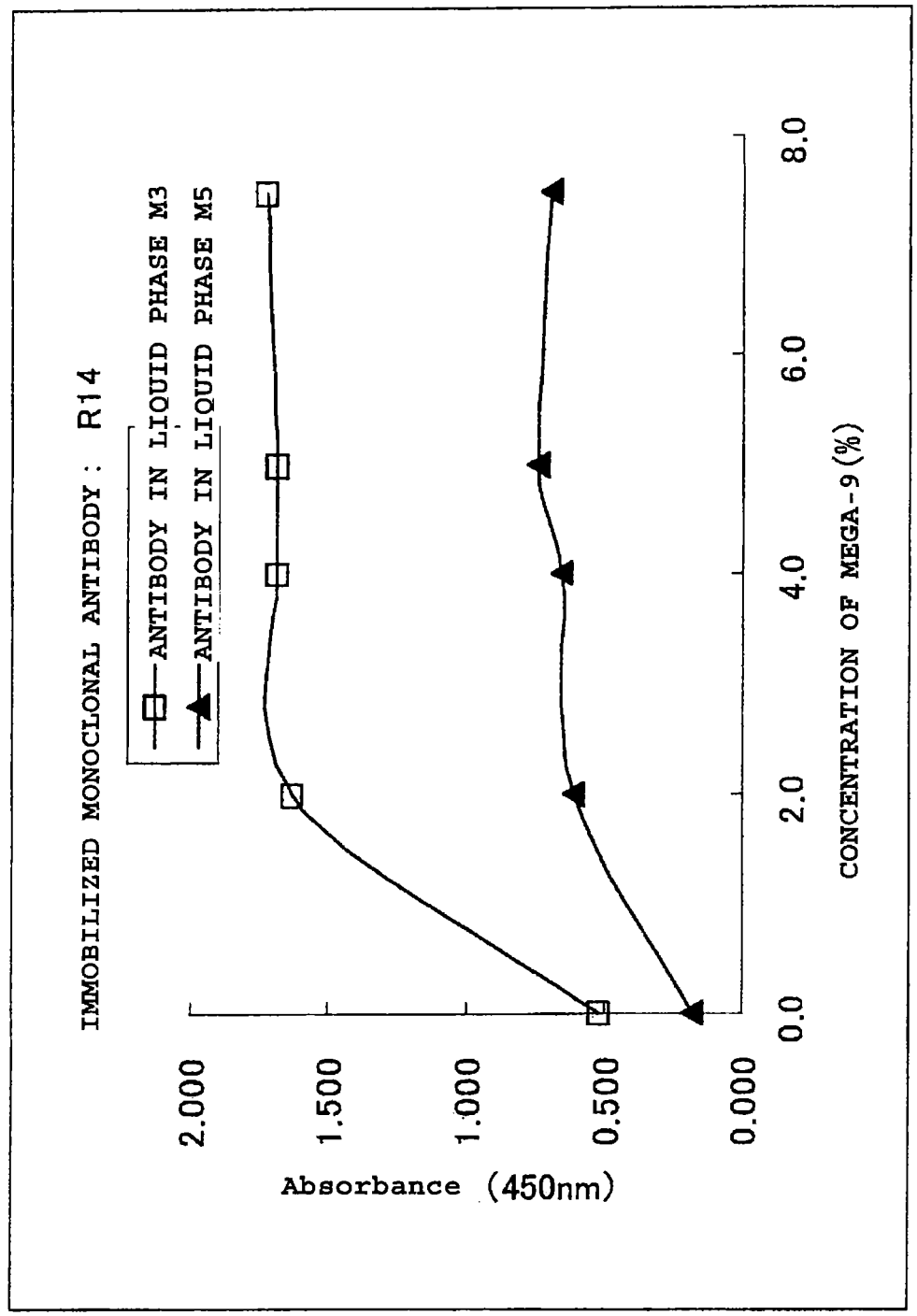
FIG. 10 shows a sandwich ELISA using the immobilized monoclonal antibody R14.
Figure 11:
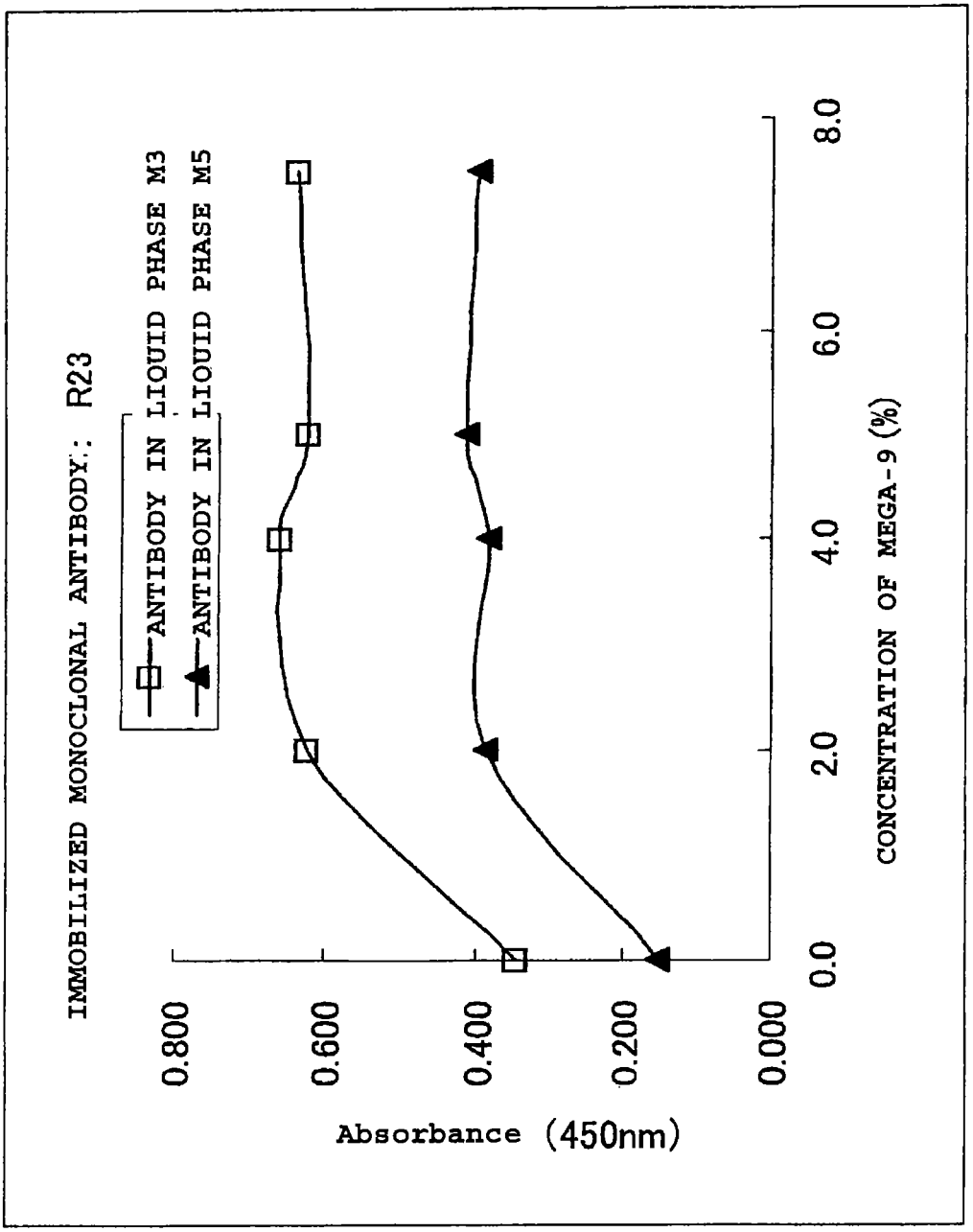
FIG. 11 shows a sandwich ELISA using the immobilized monoclonal antibody R23.

In the same manner as Example 1-5), human serum to which a solution containing the purified rabbit soluble LR11 (Lot. 070601) diluted 50- or 100-fold with PBS (PBS for blank) was added to perform reaction (the serum was diluted to obtain dilution of 8-fold at the time of the reaction) in the presence of the surfactant MEGA-9 (0%, 2.5%, 5% or 10%). As a result (see FIG. 6), almost the equivalent reaction was obtained from 2.5% to 10% MEGA-9, and it was found that the measurement of the soluble LR11 could be achieved while the influence of the serum components was avoided.

Example 3

For the combination of the monoclonal antibodies other than the combination of immobilized monoclonal antibody M3 and monoclonal antibody in liquid phase R14 in Example 2, effect of MEGA-9 (0%, 2%, 4%, 5% or 7.5%) was determined. The sample was human serum (the serum was diluted 8-fold at the time of the reaction). As a result (FIGS. 7 to 11), from all of the combinations determined, an increase in the measurement value was recognized in accordance with the addition of MEGA-9. In cases of 2% to 7.5% addition group, almost the constant value was obtained. Thus, it was found that, without being limited to a combination of specific kinds of antibodies, the measurement of the soluble LR11 might be achieved by the addition of the surfactant while the influence of the serum components was avoided.

Example 4

Measurement of the Soluble LR11 from Human Serum

Purified rabbit soluble LR11 (Lot. 071120) and highly pure bovine serum albumin with known protein concentration were subjected to SDS-polyacrylamide gel electrophoresis followed by silver staining. Thereafter, the stained image was analyzed by densitometry. As a result, the concentration of the LR11 in the rabbit soluble LR11 (Lot. 071120) was calculated to be 3.0 μg/mL. Thus-obtained purified rabbit soluble LR11 with known concentration value was used as a standard material for obtaining the concentration in human serum according to the following method.

To a micro plate (manufactured by NUNC®), monoclonal antibody M3 which had been diluted with PBS to have 5 μg/mL was added (100 μL per well), and the immobilization was carried out at room temperature for 2 hrs. After washing with PBST, BSA-PBST was added (200 μL per well) to perform blocking at room temperature for 1 hr.

After washing with PBST, three samples of human serum which had been diluted 32-, 16-, 8- or 4-fold with PBS were added (100 μL per well) in the presence of 5% MEGA-9 to the overnight reaction at room temperature (15° C. to 25° C.).

Thereafter, a standard antibody solution in which biotinylated monoclonal antibody R14 had been diluted with BSA-PBST to have 0.4 μg/mL was added (100μ per well) for the reaction for 4 hrs at room temperature. After washing with PBST, peroxidase-labeled streptavidin (manufactured by Pierce Company) which had been diluted with BSA-PBST to have concentration of 0.2 μg/mL was added to the above (100 μL per well) for the reaction at room temperature for 1 hr.

Subsequently, after washing with PBST, the TMB substrate solution was added (100 μL per well) to allow the color development for 30 min at room temperature. Then, 1.5 N sulfuric acid was added in an amount of 100 μL per well to stop the color development. Then, the measurement was carried out by using a micro plate reader (Abs. 450 nm).

Figure 12:
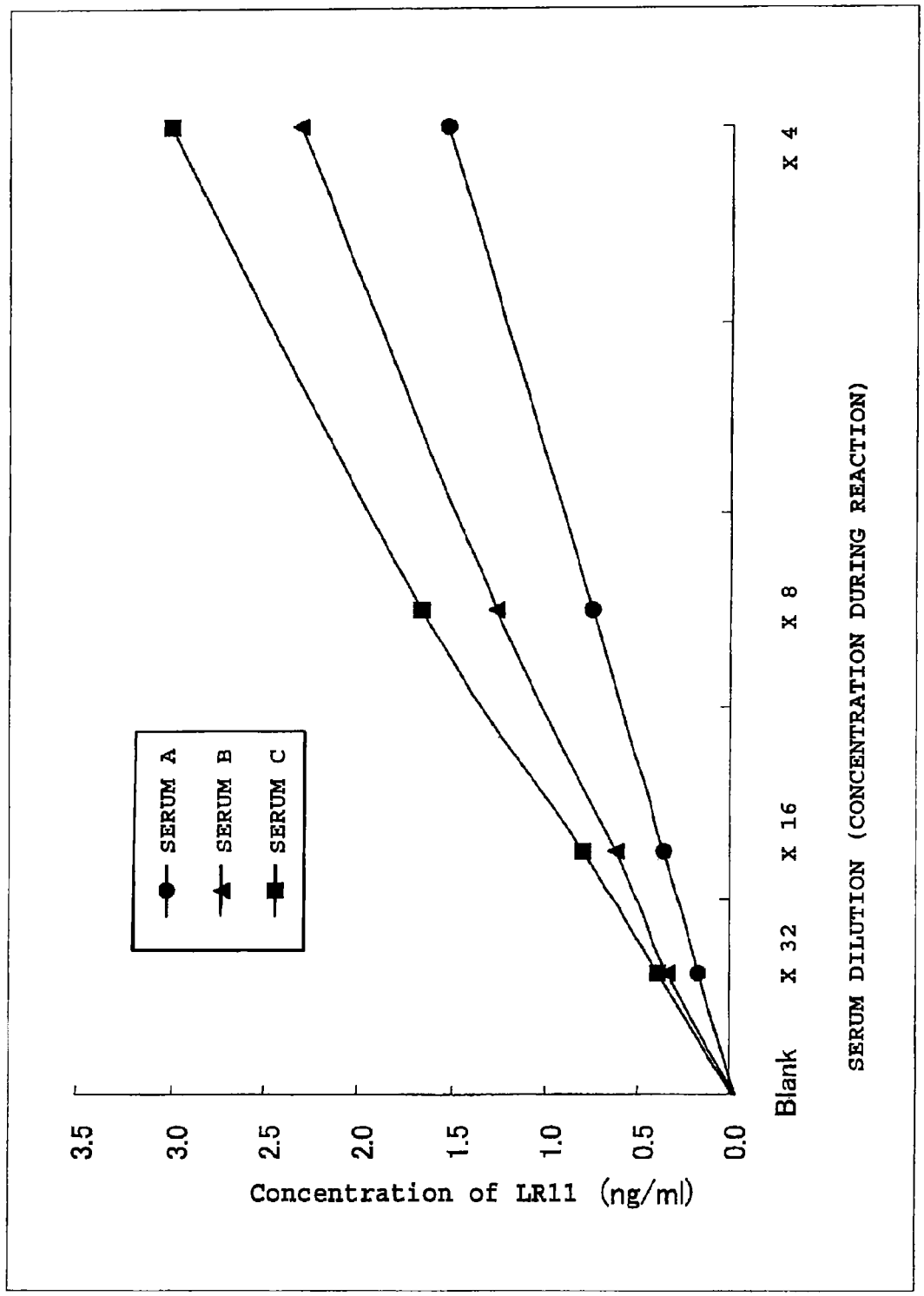
FIG. 12 shows a measurement of soluble LR11 in human serum.

As a result (FIG. 12), in the case of the treatment with MEGA-9, a reaction which is dependent on the diluted concentration of the serum, i.e., a reaction which is dependent on the LR 11 concentration in the serum, was obtained from all of the three serum samples. With respect to the value converted in terms of the LR11 concentration obtained, good dilution linearity was observed in the serum dilution range between 32-fold and 8-fold.

Example 5

Measurement of the Soluble LR11 from Serum of a Mammal Other than Human

In view of the measurement method of Example 4, each serum obtained from rabbit, monkey, goat and pig was treated with MEGA-9 and subjected to the measurement by sandwich ELISA.

Figure 13:
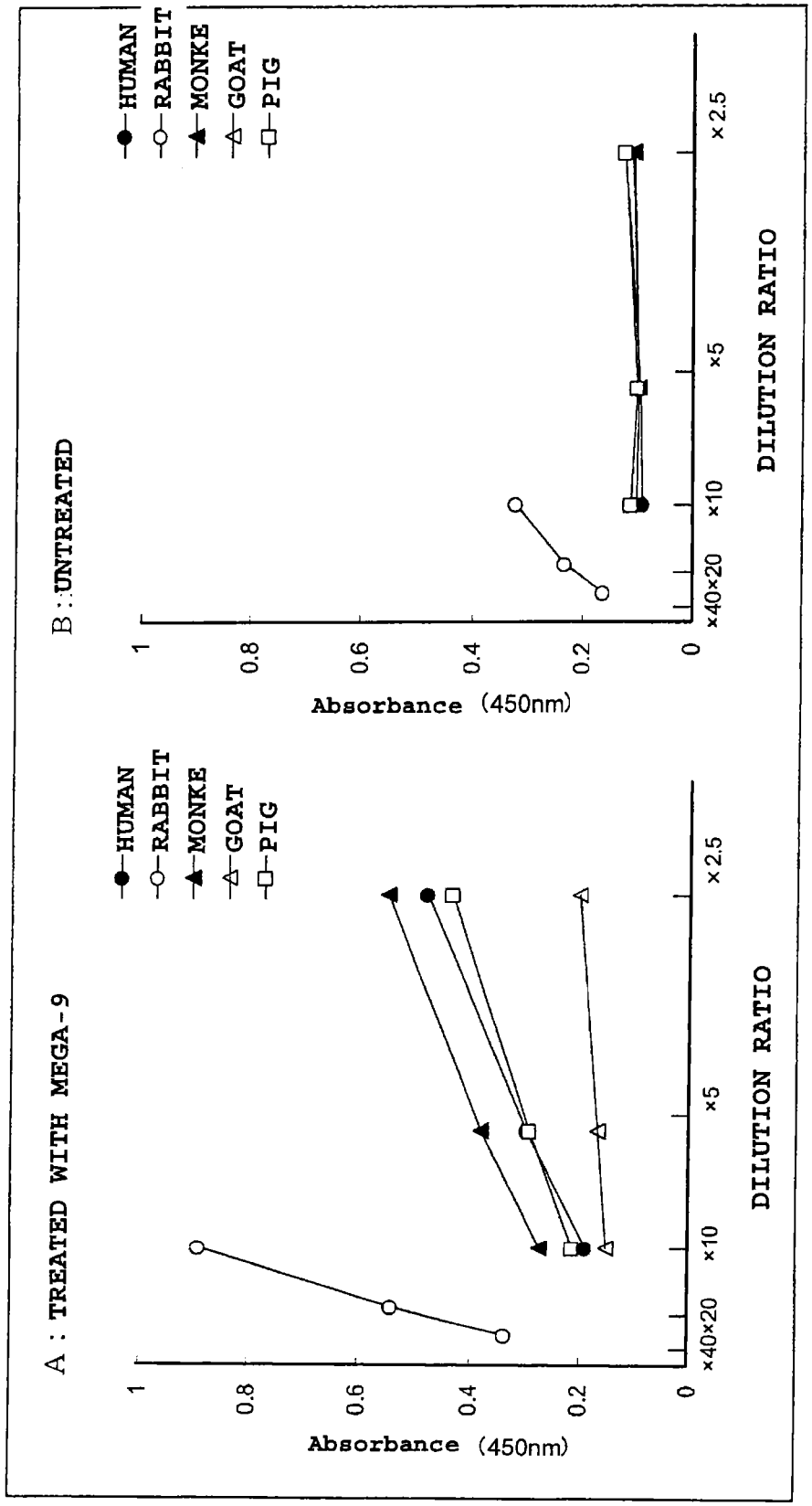
FIG. 13 shows a measurement of soluble LR11 in serum of various mammals (A: treated with MEGA-9, B: not treated).

As a result, from any of the cases above, good dilution linearity was observed like the human serum (FIG. 13A). Meanwhile, when the treatment with MEGA-9 was not carried out, basically no absorbance increase was observed from the serum of the monkey, goat and pig. In the case of the rabbit serum, the absorbance increase was observed. However, the absorbance increase ratio was significantly lower than the case wherein MEGA-9 treatment was carried out (FIG. 13B).

Example 6

Measurement of the Soluble LR11 from Human Cerebrospinal Fluid

Having the purified rabbit soluble LR11 with the previously calculated value of Example 4 as a standard material, concentration of the soluble LR11 in diluted human cerebrospinal fluid was obtained according to the method shown below.

To a micro plate (manufactured by NUNC®), monoclonal antibody M3 which had been diluted with PBS to have 10 μg/mL was added (100 μL per well), and the immobilization was carried out at room temperature for 2 hrs. After washing with PBST, BSA-PBST containing 10% sucrose was added in an amount of 200 μL per well to blocking at room temperature for 1 hr. After aspirating off the blocking solution, the plate was dried.

To the above, three samples of human cerebrospinal fluid which had been diluted 32-, 16-, 8-, 4- or 2-fold with PBS were added (100 μL per well) in the presence of 5% MEGA-9 and reacted overnight at room temperature (15° C. to 25° C.).

Thereafter, the labeled antibody solution containing biotinylated monoclonal antibody R14 obtained by dilution with BSA-PBST to have 0.4 μg/mL was added (100 μL per well) and reacted for 4 hrs at room temperature. After washing with PBST, peroxidase-labeled streptavidin (manufactured by Pierce Company) which had been diluted with BSA-PBST to have concentration of 0.2 μg/mL was added to the above (100 μL per well) for the reaction at room temperature for 1 hr.

Subsequently, after washing with PBST, the TMB substrate solution was added (100 μL per well) to allow the color development for 30 min at room temperature. Then, 1.5 N sulfuric acid was added in an amount of 100 μL per well to stop the color development. Then, the measurement was carried out by using a micro plate reader (Abs. 450 nm).

Figure 14:
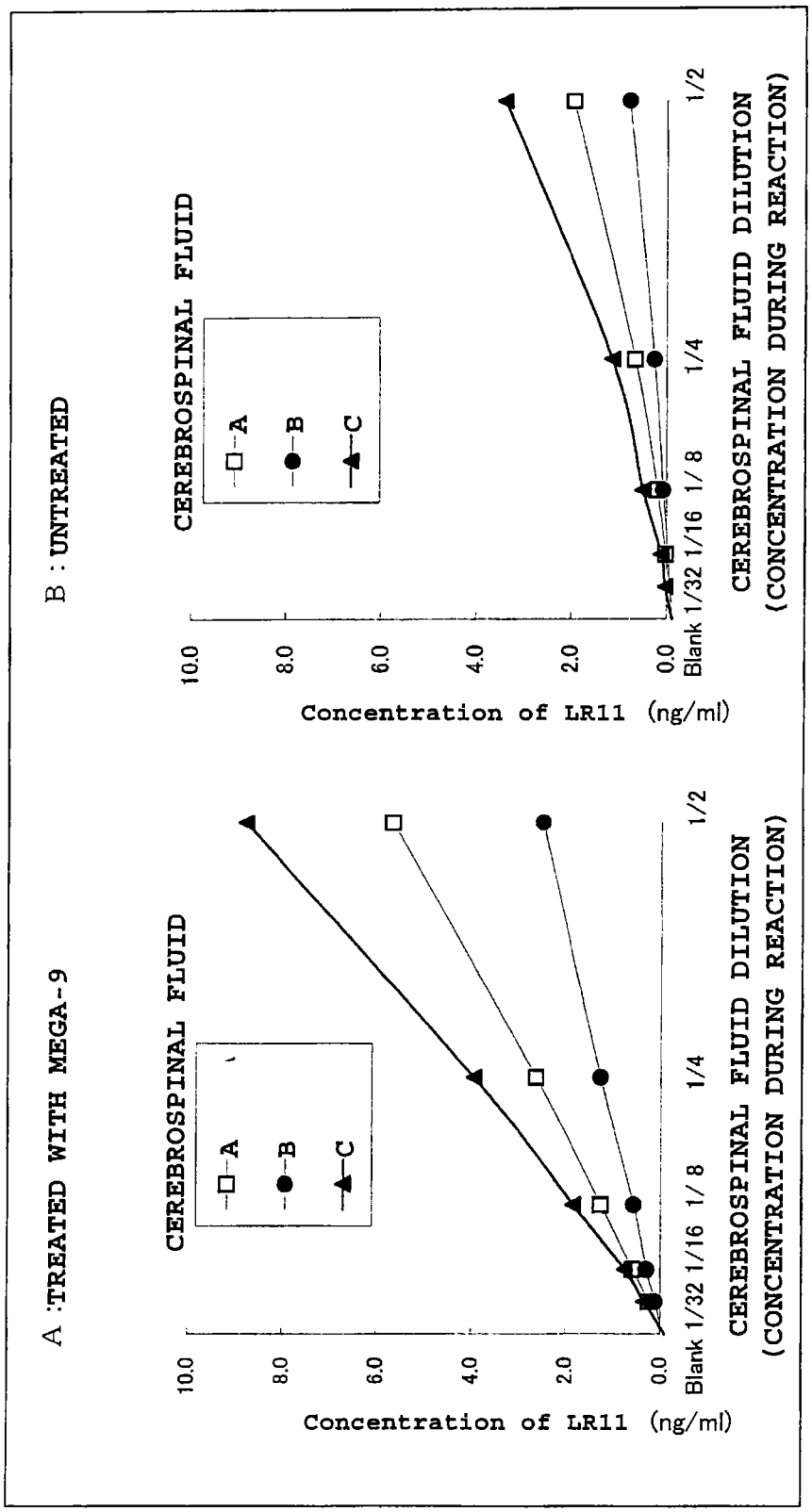
FIG. 14 shows a measurement of soluble LR11 in human cerebrospinal fluid (A: treated with MEGA-9, B: not treated).

As a result, in the case of the treatment with MEGA-9, a reaction which is dependent on the diluted concentration of the cerebrospinal fluid, i.e., a reaction which is dependent on the LR 11 concentration in the cerebrospinal fluid, was obtained from all of the three cerebrospinal fluid samples. With respect to the value converted in terms of the LR11 concentration obtained, good dilution linearity was observed in the cerebrospinal fluid dilution ratio range between 32-fold and 2-fold (FIG. 14A).

In contrast, since no sufficient absorbance increase was observed for any of the cerebrospinal fluid samples when the treatment with MEGA-9 was not carried out, it is believed that the value converted in terms of the LR11 concentration becomes a significantly small value (FIG. 14B), and therefore the accurate measurement can not be carried out.

---

The invention claimed is:

1. A method for detecting soluble LR11 in a sample comprising:
   treating a biological sample from a mammal with at least one surfactant, and
   detecting soluble LR11 directly in the treated sample;
   wherein the biological sample is serum; and
   wherein the at least one surfactant is acyl-N-methylglucamine.

2. The method of claim 1, wherein said mammal is a human.

3. The method of claim 1, wherein said mammal is a human who has or is suspected of having an arteriosclerotic disorder.

4. The method of claim 1, wherein detecting soluble LR11 in the treated sample comprises contacting the treated sample with a monoclonal antibody that binds to soluble LR11.

5. The method of claim 1, wherein detecting soluble LR11 in the treated sample comprises contacting the treated sample with a polyclonal antibody that binds to soluble LR11.

6. The method of claim 1, wherein detecting soluble LR11 in the treated sample comprises forming an immunocomplex with LR11 using at least two kinds of antibodies each having an antigen recognition site different from the other.

7. The method of claim 1, wherein detecting soluble LR11 in the treated sample is performed using immunostaining, Western blot, enzyme linked immunosorbent assay (ELISA), sandwich ELISA, immunotubidimetry (TIA or LTIA), enzyme immunoassay, chemiluminescence immunoassay, or fluorescence immunoassay.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Met Asn Glu Glu Asn Met Arg Ser Val Ile Thr Phe Asp Lys Gly
1               5                   10                  15

<210> SEQ ID NO 2
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Leu Thr Gly Leu Met Asp Met Lys Ile Phe Tyr Lys Gly Lys Asn
1               5                   10                  15

Thr Gly Ser Asn Ala Cys Val Pro Arg Pro Cys Ser Leu Leu Cys Leu
            20                  25                  30

Pro Lys Ala Asn Asn Ser Arg Ser Cys Arg Cys Pro Glu Asp Val Ser
        35                  40                  45

Ser Ser Val Leu Pro Ser Gly Asp Leu Met Cys Asp Cys Pro Gln Gly
    50                  55                  60

Tyr Gln Leu Lys Asn Asn Thr Cys Val Lys Glu Glu Asn Thr Cys Leu
65                  70                  75                  80

Arg Asn Gln Tyr Arg Cys Ser Asn Gly Asn Cys Ile Asn Ser Ile Trp
                85                  90                  95
```

```
Trp Cys Asp Phe Asp Asn Asp Cys Gly Asp Met Ser Asp Glu Arg Asn
            100                 105                 110
Cys Pro Thr Thr Ile Cys Asp Leu Asp Thr Gln Phe Arg Cys Gln Glu
        115                 120                 125
Ser Gly Thr Cys Ile Pro Leu Ser Tyr Lys Cys Asp Leu Glu Asp Asp
    130                 135                 140
Cys Gly Asp Asn Ser Asp Glu Ser His Cys Glu Met His Gln Cys Arg
145                 150                 155                 160
Ser Asp Glu Tyr Asn Cys Ser Ser Gly Met Cys Ile Arg Ser Ser Trp
                165                 170                 175
Val Cys Asp Gly Asp Asn Asp Cys Arg Asp Trp Ser Asp Glu Ala Asn
            180                 185                 190
Cys Thr Ala Ile Tyr His Thr Cys Glu Ala Ser Asn Phe Gln Cys Arg
        195                 200                 205
Asn Gly His Cys Ile Pro Gln Arg Trp Ala Cys Asp Gly Asp Thr Asp
    210                 215                 220
Cys Gln Asp Gly Ser Asp Glu Asp Pro Val Asn Cys Glu Lys Lys Cys
225                 230                 235                 240
Asn Gly Phe Arg Cys Pro Asn Gly Thr Cys Ile Pro Ser Ser Lys His
                245                 250                 255
Cys Asp Gly Leu Arg Asp Cys Ser Asp Gly Ser Asp Glu Gln His Cys
            260                 265                 270
Glu Pro Leu Cys Thr His Phe Met Asp Phe Val Cys Lys Asn Arg Gln
        275                 280                 285
Gln Cys Leu Phe His Ser Met Val Cys Asp Gly Ile Ile Gln Cys Arg
    290                 295                 300
Asp Gly Ser Asp Glu Asp Ala Ala Phe Ala Gly Cys Ser Gln Asp Pro
305                 310                 315                 320
Glu Phe His Lys Val Cys Asp Glu Phe Gly Phe Gln Cys Gln Asn Gly
                325                 330                 335
Val Cys Ile Ser Leu Ile Trp Lys Cys Asp Gly Met Asp Asp Cys Gly
            340                 345                 350
Asp Tyr Ser Asp Glu Ala Asn Cys Glu Asn Pro Thr Glu Ala Pro Asn
        355                 360                 365
Cys Ser Arg Tyr Phe Gln Phe Arg Cys Glu Asn Gly His Cys Ile Pro
    370                 375                 380
Asn Arg Trp Lys Cys Asp Arg Glu Asn Asp Cys Gly Asp Trp Ser Asp
385                 390                 395                 400
Glu Lys Asp Cys Gly Asp Ser His Ile Leu Pro Phe Ser Thr Pro Gly
                405                 410                 415
Pro Ser Thr Cys Leu Pro Asn Tyr Tyr Arg Cys Ser Ser Gly Thr Cys
            420                 425                 430
Val Met Asp Thr Trp Val Cys Asp Gly Tyr Arg Asp Cys Ala Asp Gly
        435                 440                 445
Ser Asp Glu Glu Ala Cys Pro Leu Leu Ala Asn Val Thr Ala Ala Ser
    450                 455                 460
Thr Pro Thr Gln Leu Gly Arg Cys Asp Arg Phe Glu Phe Glu Cys His
465                 470                 475                 480
Gln Pro Lys Thr Cys Ile Pro Asn Trp Lys Arg Cys Asp Gly His Gln
                485                 490                 495
Asp Cys Gln Asp Gly Arg Asp Glu Ala Asn Cys Pro Thr His Ser Thr
            500                 505                 510
```

```
Leu Thr Cys Met Ser Arg Glu Phe Gln Cys Glu Asp Gly Glu Ala Cys
        515                 520                 525
Ile Val Leu Ser Glu Arg Cys Asp Gly Phe Leu Asp Cys Ser Asp Glu
    530                 535                 540
Ser Asp Glu Lys Ala Cys Ser
545                 550
```